(12) United States Patent
Li et al.

(10) Patent No.: US 12,029,829 B2
(45) Date of Patent: Jul. 9, 2024

(54) BIOCOMPATIBLE ADHESIVES AND METHODS OF USE THEREOF

(71) Applicant: President and Fellows of Harvard College, Cambridge, MA (US)

(72) Inventors: Jianyu Li, Verdun (CA); Adam D. Celiz, Braintree (GB); David J. Mooney, Sudbury, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 16/086,631

(22) PCT Filed: Mar. 22, 2017

(86) PCT No.: PCT/US2017/023538
§ 371 (c)(1),
(2) Date: Sep. 20, 2018

(87) PCT Pub. No.: WO2017/165490
PCT Pub. Date: Sep. 28, 2017

(65) Prior Publication Data
US 2019/0091367 A1  Mar. 28, 2019

Related U.S. Application Data

(60) Provisional application No. 62/356,939, filed on Jun. 30, 2016, provisional application No. 62/311,646, filed on Mar. 22, 2016.

(51) Int. Cl.
*A61L 24/00* (2006.01)
*A61K 9/70* (2006.01)
*A61L 24/04* (2006.01)

(52) U.S. Cl.
CPC ........ *A61L 24/0031* (2013.01); *A61K 9/7046* (2013.01); *A61K 9/7061* (2013.01); *A61K 9/7069* (2013.01); *A61L 24/0015* (2013.01); *A61L 24/043* (2013.01); *A61L 2400/04* (2013.01); *A61L 2400/06* (2013.01); *A61L 2420/02* (2013.01)

(58) Field of Classification Search
None
See application file for complete search history.

(56) References Cited

U.S. PATENT DOCUMENTS

| | | | |
|---|---|---|---|
| 3,611,732 A | 10/1971 | Epstein | |
| 4,768,523 A | 9/1988 | Cahalan et al. | |
| 5,334,640 A | 8/1994 | Desai et al. | |
| 5,563,186 A | 10/1996 | Thompson | |
| 5,620,702 A | 4/1997 | Podell et al. | |
| 5,644,049 A | 7/1997 | Giusti et al. | |
| 6,030,634 A | 2/2000 | Wu et al. | |
| 6,271,278 B1 | 8/2001 | Park et al. | |
| 6,352,707 B1 | 3/2002 | Usala | |
| 6,960,617 B2 | 11/2005 | Omidian et al. | |
| 8,293,510 B2 | 10/2012 | Detamore et al. | |
| 9,387,276 B2 | 7/2016 | Sun et al. | |
| 9,987,221 B2 | 6/2018 | Richard | |
| 10,383,980 B2 | 8/2019 | Sun et al. | |
| 2003/0232895 A1 | 12/2003 | Omidian et al. | |
| 2008/0139694 A1 | 6/2008 | Ratcliffe | |
| 2008/0317818 A1 | 12/2008 | Griffith et al. | |
| 2010/0021416 A1 | 1/2010 | Lichter et al. | |
| 2010/0055184 A1 | 3/2010 | Zeitels et al. | |
| 2010/0234784 A1 | 9/2010 | Hartwell | |
| 2012/0009223 A1 | 1/2012 | Wenguang et al. | |
| 2013/0172419 A1 | 7/2013 | Saxena et al. | |
| 2014/0295553 A1* | 10/2014 | Du ........................ | C12M 23/10 435/377 |
| 2015/0038613 A1 | 2/2015 | Sun et al. | |
| 2017/0197392 A1 | 7/2017 | Illeperuma et al. | |
| 2017/0202789 A1 | 7/2017 | Sexton et al. | |
| 2020/0000967 A1 | 1/2020 | Sun et al. | |
| 2021/0338577 A1 | 11/2021 | Freedman et al. | |
| 2021/0353830 A1 | 11/2021 | Sun et al. | |
| 2024/0016972 A1 | 1/2024 | Freedman et al. | |

FOREIGN PATENT DOCUMENTS

| | | |
|---|---|---|
| FR | 2938544 A1 | 5/2010 |
| JP | 2005-110537 A | 4/2005 |
| JP | 2009-507110 A | 2/2009 |
| JP | 2009-120855 A | 6/2009 |
| KR | 20100096676 A | 9/2010 |
| WO | 1998/012228 A1 | 3/1998 |
| WO | 1998/52543 A1 | 11/1998 |

(Continued)

OTHER PUBLICATIONS

Duan et al. (J Mol Genet Med, 9(3), 1-3, 2015) Double-Network Carboxymethyl Chitosan Grafting . . . .*
Picart et al. (Adv. Funct. Mater. 2005, 15, 1771-1780) Controlled Degradability of Polysaccharide . . . .*
Kong et al. (Biomacromolecules 2004, 5, 1720-1727) Controlling Rigidity and Degradation of Alginate Hydrogels . . . .*
Shariatinia (International Journal of Biological Macromolecules 120 (2018) 1406-1419) Carboxymethyl chitosan: Properties and biomedical applications.*
Li et al. (ACS Macro Lett. 2014, 3, 520-523,) Hybrid Hydrogels with Extremely High Stiffness and Toughness.*

(Continued)

*Primary Examiner* — Tigabu Kassa
(74) *Attorney, Agent, or Firm* — McCarter & English, LLP

(57) ABSTRACT

The present invention is directed to a biocompatible adhesive system comprising a) a hydrogel comprising a first polymer network and a second polymer network, wherein the first polymer network comprises covalent crosslinks and the second polymer network comprises ionic crosslinks; b) a high density primary amine polymer; and c) a coupling agent. The present invention also provides methods preparing and using the biocompatible adhesive system.

11 Claims, 24 Drawing Sheets

(56) References Cited

FOREIGN PATENT DOCUMENTS

| WO | WO 03/089506 | * | 10/2003 |
|---|---|---|---|
| WO | 2007/028258 A2 | | 3/2007 |
| WO | 2009/134414 A1 | | 11/2009 |
| WO | 2010/093528 A2 | | 8/2010 |
| WO | 2013/025763 A2 | | 2/2013 |
| WO | 2013/103956 A1 | | 7/2013 |
| WO | 2015/143078 A1 | | 9/2015 |
| WO | 2015/154078 A1 | | 10/2015 |
| WO | WO 2015/154078 | * | 10/2015 |
| WO | 2016/007429 A1 | | 1/2016 |
| WO | 2016/100355 A1 | | 6/2016 |
| WO | 2017/165490 A1 | | 9/2017 |
| WO | 2019/203974 A1 | | 10/2019 |
| WO | 2020/077173 A1 | | 4/2020 |

OTHER PUBLICATIONS

Cohen et al., Gelatin-alginate novel tissue adhesives and their formulation-strength effects. Acta Biomater. Nov. 2013;9(11):9004-11.
Ishihara et al., Photocrosslinkable chitosan as a dressing for wound occlusion and accelerator in healing process. Biomaterials. Feb. 2002;23(3):833-40.
Yuk et al., Tough bonding of hydrogels to diverse non-porous surfaces. Nat Mater. Feb. 2016;15(2):190-6.
International Search Report and Written Opinion for Application No. PCT/US2017/023538, dated Jun. 9, 2017. 12 pages.
Li et al., Hybrid Hydrogels with Extremely High Stiffness and Toughness. ACS Macro Lett. 2014;3:520-523.
Braun et al., The relative contribution of calcium, zinc and oxidation-based cross-links to the stiffness of Arion subfuscus glue. J Exp Biol. Apr. 15, 2013;216(Pt 8):1475-83.
Gilles et al., Stability of water-soluble carbodiimides in aqueous solution. Anal Biochem. Feb. 1, 1990;184(2):244-8.
Nakajima et al., Mechanism of amide formation by carbodiimide for bioconjugation in aqueous media. Bioconjug Chem. Jan.-Feb. 1995;6(1):123-30.
Sun et al., Highly stretchable and tough hydrogels. Nature. Sep. 6, 2012;489(7414):133-6.
Supplementary European Search Report for Application No. 17771037.3, dated Oct. 31, 2019, 9 pages.
Bakarich et al., Recovery from applied strain in interpenetrating polymer network hydrogels with ionic and covalent cross-links. Soft Matter. Sep. 2012;8:9985-8.
Naficy et al., Mechanical properties of interpenetrating polymer network hydrogels based ionically and covalently crosslinked networks. J Appl Polym Sci. Nov. 2013;130(4):2504-13.
Haug et al., The Effect of Divalent Metals on the Properties of Alginate Solutions. II. Comparison of Different Metal Ions. Acta Chemica Scandinavica. 1965;19;341-51.
Leo et al., Effects of sterilization treatments on some properties of alginate solutions and gels. Biotechnol Prog. Jan.-Feb. 1990;6(1):51-3.
Omidian et al., Elastic, superporous hydrogel hybrids of polyacrylamide and sodium alginate. Macromol Biosci. Sep. 15, 2006;6(9):703-10.

Park et al., Biodegradable Hydrogels for Drug Delivery. Technomic Publishing Company, Inc., Lancaster, Pennsylvania. p. 48, (1993).
Tsujino et al., A new unsaturated uronide isolated from alginase hydrolysate. Nature. Dec. 9, 1961;192:970-1.
International Search Report and Wristten Opinion for Application No. PCT/US2019/055779, dated Dec. 30, 2019, 11 pages.
International Search Report and Written Opinion for Application No. PCT/US2013/020518, dated Mar. 11, 2013, 12 pages.
U.S. Appl. No. 16/459,907, filed Jul. 2, 2019, 2020-0000967, Allowed.
George et al., Polyionic hydrocolloids for the intestinal delivery of protein drugs: alginate and chitosan—a review. J Control Release. Aug. 10, 2006;114(1):1-14.
U.S. Appl. No. 14/370,451, filed Jul. 2, 2014, U.S. Pat. No. 9,387,276, Issued.
U.S. Appl. No. 15/172,549, filed Jun. 3, 2016, U.S. Pat. No. 10,383,980, Issued.
U.S. Appl. No. 16/459,907, filed Jul. 2, 2019, U.S. Pat. No. 11,033,658, Issued.
U.S. Appl. No. 17/320,726, filed May 14, 2021, 2021-0353830, Published.
U.S. Appl. No. 17/283,412, filed Apr. 7, 2021, 2021-0338577, Published.
Choi et al., Depolymerization of Alginates by Hydrogen Peroxide/Ultrasonic Irradiation. Polymer(Korea). 2011;35 (5):444-450.
Park et al., Types of Biodegradable Hydrogels. Biodegradable Hydrogels for Drug Delivery. Technomic Publishing Company, Inc., Lancaster, Pennsylvania. Chapter 3, pp. 35-66, (1993).
Aguzzi et al., Use of clays as drug delivery systems: Possibilities and limitations. Applied Clay Science. 2007;36:22-36.
Farahmandghavi et al., Silicone matrices loaded with levonorgestrel particles: Impact of the particle size on drug release. Journal of Drug Delivery Science and Technology. 2019;49:132-142.
Hong et al., 3D Printing of Highly Stretchable and Tough Hydrogels into Complex, Cellularized Structures. Adv Mater. Jul. 15, 2015;27(27):4035-40.
Li et al., Novel Poly(N-isopropylacrylamide)/Clay/Poly(acrylamide) IPN Hydrogels with the Response Rate and Drug Release Controlled by Clay Content. J Polym Sci Part B: Polym Phys. 2009;47:96-106.
Li et al., Tough adhesives for diverse wet surfaces. Science. Jul. 28, 2017;357(6349):378-381.
International Search Report and Written Opinion for Application No. PCT/US2020/051427, dated Feb. 4, 2021, 11 pages.
U.S. Appl. No. 14/370,451, U.S. Pat. No. 9,387,276, filed Jul. 2, 2014, Issued.
U.S. Appl. No. 15/172,549, U.S. Pat. No. 10,383,980, filed Jun. 3, 2016, Issued.
U.S. Appl. No. 16/459,907, U.S. Pat. No. 11,033,658, filed Jul. 2, 2019, Issued.
U.S. Appl. No. 17/320,726, Publication No. 2021-0353830, filed May 14, 2021, Abandoned.
U.S. Appl. No. 17/283,412, Publication No. 2021-0338577, filed Apr. 7, 2021, Allowed.
U.S. Appl. No. 17/761,193, Publication No. 2024-0016972, filed Mar. 17, 2022, Published.

* cited by examiner

BIOCOMPATIBLE ADHESIVES AND METHODS OF USE THEREOF

CROSS REFERENCE TO RELATED APPLICATION

This application claims priority to U.S. Provisional Application Ser. No. 62/356,939 filed on Jun. 30, 2016; and U.S. Provisional Application Ser. No. 62/311,646 filed on Mar. 22, 2016. The entire contents of each of these applications are incorporated herein by reference.

GOVERNMENT SUPPORT

This invention was made with government support under DE013033 awarded by National Institute of Health (NIH). The government has certain rights in this invention.

BACKGROUND OF THE INVENTION

Tissue adhesives can be used following minimally invasive surgery. However, the current array of tissue adhesives do not meet the requirements in the clinics. For example, current clinically available tissue adhesives like cyanoacrylate can be either toxic, or poorly adhesive on wet surfaces with blood such that they debond easily under in vivo dynamic environments. The formation of tissue adhesion is often complicated under in vivo conditions due to exposure to liquids (e.g., blood), and dynamic movements of tissues. An ideal tissue adhesive needs (1) to attach strongly to wet living tissues independent of blood; (2) to sustain significant mechanical loads without failure; (3) to adhere selectively to prevent unwanted adhesion; (4) to be biocompatible, non-toxic and tunable in degradation rate.

Therefore, there remains an unmet need for tissue adhesives that exhibit strong bonding to the desired surface in particular wet surfaces of biological tissues, can withstand significant mechanical stresses and strains, and are biocompatible.

SUMMARY OF THE INVENTION

The present invention is based, at least in part, on the discovery of certain novel biocompatible adhesives (i.e., biocompatible adhesive systems) that are capable of adhering to a biological surface (e.g., tissue or device) and remaining in place even in a wet and dynamic environment. In particular, the present inventors have surprisingly discovered that the non-toxic biocompatible adhesives disclosed herein exhibit strong and selective adhesion to the target surface (e.g., tissue or device), even in wet and/or dynamic environments. In addition, the biocompatible adhesives disclosed herein can sustain significant mechanical loads without failure and have an elastomeric interface that enables large deformation of the adhesive. Furthermore, the biocompatible adhesives have tunable degradation properties, permitting degradation of the material to occur naturally. The biocompatible adhesives disclosed in the present invention lead to extremely high adhesion energy (>1000 J/m$^2$) on wet surfaces like biological tissues than all existing adhesives. Adhesion is fast (within minutes), independent of blood exposure, and compatible with in vivo dynamic movements (e.g., beating heart). The biocompatible adhesives can be in the form of preformed patches or injectable solutions that can be in situ cured on the target surface (e.g., can act as a surgical glue providing a suture-less adhesive).

Accordingly, in one aspect, the present invention provides a biocompatible adhesive system comprising a) a hydrogel comprising a first polymer network and a second polymer network, wherein the first polymer network comprises covalent crosslinks and the second polymer network comprises ionic crosslinks; b) a high density primary amine polymer; and c) a coupling agent. The synergistic effect from the three components leads to a biocompatible adhesive combining tough bulk matrix and extremely adhesive surfaces.

In some embodiments, the present invention provides a biocompatible adhesive system comprising a) a hydrogel comprising a first polymer network and a second polymer network, wherein the first polymer network comprises covalent crosslinks and the second polymer network comprises ionic crosslinks; b) a high density primary amine polymer; and c) a coupling agent, wherein the high density primary amine polymer and coupling agent are applied to one side of the hydrogel.

In some embodiments, the first polymer network is selected from the group consisting of polyacrylamide, poly(vinyl alcohol) (PVA), polyethylene glycol (PEG), polyphosphazene, collagen, gelatin, poly(acrylate), poly(methacrylate), poly(methacrylamide), poly(acrylic acid), poly(N-isopropylacrylamide), poly(N,N-dimentylacrylamide), poly(allylamine) and copolymers thereof. In a particular embodiment, the first polymer network is polyethylene glycol (PEG).

In some embodiments, the first polymer network is selected from the group consisting of polyacrylamide, poly(hydroxyethylmethacrylate) (PHEMA), poly(vinyl alcohol) (PVA), polyethylene glycol (PEG), polyphosphazene, collagen, gelatin, poly(acrylate), poly(methacrylate), poly(methacrylamide), poly(acrylic acid), poly(N-isopropylacrylamide) (PNIPAM), poly(N,N-dimentylacrylamide), poly(allylamine) and copolymers thereof. In a particular embodiment, the first polymer network is polyethylene glycol (PEG), which can form a covalently cross-linked polymeric network via free-radical polymerization, click chemistry, etc.

In some embodiments, the second polymer network is selected from the group consisting of alginate, pectate, carboxymethyl cellulose, oxidized carboxymethyl cellulose, hyaluronate, chitosan, κ-carrageenan, ι-carrageenan and λ-carrageenan, wherein the alginate, carboxymethyl cellulose, hyaluronate chitosan, κ-carrageenan, ι-carrageenan and λ-carrageenan are each optionally oxidized, wherein the alginate, carboxymethyl cellulose, hyaluronate chitosan, κ-carrageenan, ι-carrageenan and λ-carrageenan optionally include one or more groups selected from the group consisting of methacrylate, acrylate, acrylamide, methacrylamide, thiol, hydrazine, tetrazine, norbornene, transcyclooctene and cyclooctyne. In a particular embodiment, the second polymer network comprises alginate. In some embodiments, the alginate is comprised of a mixture of a high molecular weight alginate and a low molecular weight alginate. In a certain embodiments, the ratio of the high molecular weight alginate to the low molecular weight alginate is about 5:1 to about 1:5.

In some embodiments, the first polymer network and the second polymer network are covalently coupled.

In some embodiments, the hydrogel comprises about 30% to about 98% water.

In some embodiments, the hydrogel is fabricated in the form of a patch.

In some embodiments, the high density primary amine polymer comprises at least one primary amine per monomer unit. In certain embodiments, the high density primary amine polymer is selected from the group consisting of chitosan, gelatin, collagen, polyallylamine, polylysine, and polyethylenimine.

In some embodiments, the coupling agent includes a first carboxyl activating agent. In certain embodiments, the first carboxyl activating agent is a carbodiimide. In particular embodiments, the carbodiimide is selected from the group consisting of 1-ethyl-3-(3-dimethylaminopropyl)carbodiimide (EDC, EDAC or EDCI), dicyclohexylcarbodiimide (DCC) and diisopropylcarbodiimide (DIC). In some embodiments, the coupling agent further includes a second carboxyl activating agent. In certain embodiments, the second carboxyl activating agent is N-hydroxysuccinimide (NHS), N-hydroxysulfosuccinimide (sulfo-NHS), hydroxybenzotriazole (HOBt), dimethylaminopyridine (DMAP), Hydroxy-3,4-dihydro-4-oxo-1,2,3-benzotriazine (HOOBt/HODhbt), 1-Hydroxy-7-aza-1H-benzotriazole (HOAt), Ethyl 2-cyano-2-(hydroximino)acetate, Benzotriazol-1-yloxy-tris(dimethylamino)-phosphonium hexafluorophosphate (BOP), Benzotriazol-1-yloxy-tripyrrolidino-phosphonium hexafluorophosphate, 7-Aza-benzotriazol-1-yloxy-tripyrrolidinophosphonium hexafluorophosphate), Ethyl cyano(hydroxyimino)acetato-$O^2$)-tri-(1-pyrrolidinyl)-phosphonium hexafluorophosphate, 3-(Diethoxy-phosphoryloxy)-1,2,3-benzo[d] triazin-4(3H)-one, 2-(1H-Benzotriazol-1-yl)-N,N,N',N'-tetramethylaminium tetrafluoroborate/hexafluorophosphate, 2-(6-Chloro-1H-benzotriazol-1-yl)-N,N,N',N'-tetramethylaminium hexafluorophosphate), N-[(5-Chloro-1H-benzotriazol-1-yl)-dimethylamino-morpholino]-uronium hexafluorophosphate N-oxide, 2-(7-Aza-1H-benzotriazol-1-yl)-N,N,N',N'-tetramethylaminium hexafluorophosphate, 1-[1-(Cyano-2-ethoxy-2-oxoethylideneaminooxy)-dimethylamino-morpholino]-uronium hexafluorophosphate, 2-(1-Oxy-pyridin-2-yl)-1,1,3,3-tetramethylisothiouronium tetrafluoroborate, Tetramethylfluoroformamidinium hexafluorophosphate, N-Ethoxycarbonyl-2-ethoxy-1,2-dihydroquinoline, 2-Propanephosphonic acid anhydride, 4-(4,6-Dimethoxy-1,3,5-triazin-2-yl)-4-methylmorpholinium salts, (bis-Trichloromethylcarbonate, 1,1'-Carbonyldiimidazole.

In some embodiments, the high density primary amine polymer and the coupling agent are packaged separately. In certain embodiments, the high density primary amine polymer is in a solution and the coupling agent is in solid form. In some embodiments, the coupling agent is added to the high density primary amine polymer solution. In some embodiments, the concentration of the high density primary amine polymer in the solution is about 0.1% to about 50%. In certain embodiments, the coupling agent includes at least a first carboxyl activating agent and optionally a second carboxyl activating agent, and wherein the concentration of the first carboxyl activating agent in the solution is about 3 mg/mL to about 50 mg/mL. In some embodiments, the high density primary amine polymer is in a solution, the coupling agent is added to the high density primary amine polymer solution, and the solution is applied to the hydrogel.

In some embodiments, the system further comprises a first therapeutically active agent. In certain embodiments, the first therapeutically active agent is encapsulated in or attached to the surface of the hydrogel. In some embodiments, the first therapeutically active agent is encapsulated in or attached to the surface of the high density primary amine polymer.

In certain embodiments, the system further comprises a second therapeutically active agent. In some embodiments, the second therapeutically active agent is encapsulated in or attached to the surface of the hydrogel. In some embodiments, the second therapeutically active agent is encapsulated in or attached to the surface of the high density primary amine polymer. In some embodiments, the first and second therapeutically active agents are independently selected from the group consisting of a small molecule, a biologic, a nanoparticle, and a cell. In certain embodiments, the biologic is selected from the group consisting of a growth factor, an antibody, a vaccine, a cytokine, a chemokine, a hormone, a protein, and a nucleic acid.

In some embodiments, a device is encapsulated with the hydrogel and the high density primary amine polymer and coupling agent are applied to the exterior surface of the hydrogel encapsulating the device. In certain embodiments, the device is a medical device selected from the group consisting of a defibrillator, a pacemaker, a stent, a catheter, a tissue implant, a screw, a pin, a plate, a rod, an artificial joint, a pneumatic actuator, a sensor, an elastomer-based device, and a hydrogel based device.

In some embodiments, the system is characterized by an interfacial toughness of from about 100 J/m$^2$ to 5000 J/m$^2$.

In some embodiments, the system is transparent.

In some embodiments, the system is suitable for application to a surface that is wet, dynamic, or a combination of wet and dynamic.

In some embodiments, the system is suitable for injection into a subject.

In some embodiments, the present invention is directed to a biocompatible adhesive system including: a) a hydrogel comprising a first polymer network and a second polymer network, wherein said first polymer network comprises covalent crosslinks and the second polymer network comprises ionic crosslinks, wherein the first network comprises a polymer selected from the group consisting of polyacrylamide, poly(vinyl alcohol) (PVA), polyethylene glycol (PEG), and polyphosphazene; and the second network comprises an alginate polymer; b) a high density primary amine polymer selected from the group consisting of chitosan, gelatin, collagen, polyallylamine, polylysine, and polyethylamine; and c) a coupling agent comprising 1-ethyl-3-(3-dimethylaminopropyl)carbodiimide (EDC, EDAC or EDCI) and optionally N-hydroxysuccinimide (NHS).

In another aspect, the present invention provides a method of adhering a hydrogel to a surface (e.g., tissue or device), the method including the steps of a) applying a solution comprising a high density primary amine polymer and a coupling agent to the hydrogel; and b) placing the hydrogel on the surface; wherein the hydrogel comprises a first polymer network and a second polymer network, wherein the first polymer network comprises covalent crosslinks and the second polymer network comprises ionic crosslinks. In some embodiments, the surface is a tissue. In certain embodiments, the tissue is selected from the group consisting of heart tissue, skin tissue, blood vessel tissue, bowel tissue, liver, kidney, pancreas, lung, trachea, eye, cartilage tissue, and tendon tissue. In certain embodiments, the surface is a medical device. In some embodiments, the hydrogel encapsulates the medical device. In some embodiments, the medical device selected from the group consisting of a defibrillator, a pacemaker, a stent, a catheter, a tissue implant, a screw, a pin, a plate, a rod, an artificial joint, a pneumatic actuator, a sensor, an elastomer-based device, and a hydrogel based device. In certain embodiments, the hydrogel is adhered to a surface in order to close a wound. In some embodiments, the hydrogel is adhered to a surface in order to repair a heart defect.

In another aspect, the present invention provides a method of delivering a therapeutically active agent to a subject, the method including a) applying a solution comprising a high density primary amine polymer and a coupling agent to a hydrogel; and b) placing the hydrogel on the surface (e.g., tissue or device); wherein the hydrogel comprises a first polymer network and a second polymer network, wherein the first polymer network comprises covalent crosslinks and the second polymer network comprises ionic crosslinks, and wherein at least one therapeutically active agent is encapsulated in, or attached to the surface of, the hydrogel and/or high density primary amine polymer, thereby delivering a therapeutically active agent to the subject.

In some embodiments, the first polymer network is modified with two reactive moieties, wherein the reactive moieties are each independently selected from the group consisting of methacrylate, acrylate, acrylamide, methacrylamide, thiol, hydrazine, tetrazine, norbornene, transcyclooctene and cyclooctyne. In some embodiments, the second polymer network is alginate. In some embodiments, the first polymer network is polyethylene glycol (PEG) modified with norborne and polyethylene glycol (PEG) modified with tetrazine. In some embodiments, the two reactive moieties react in the presence of $Ca^{2+}$ (e.g., $CaSO_4$). In some embodiments, the two reactive moieties react in the presence of UV light.

The present invention is illustrated by the following drawings and detailed description, which do not limit the scope of the invention described in the claims.

BRIEF DESCRIPTION THE DRAWINGS

The patent or application file contains at least one drawing executed in color. Copies of this patent or patent application publication with color drawing(s) will be provided by the Office upon request and payment of the necessary fee.

FIG. 1 is a chart comparing the interfacial toughness of a high density primary amine polymer ("bridging polymer", chitosan) in the presence and absence of a EDC/NHS (coupling agent) (top) and a chart showing the increase in interfacial toughness of the biocompatible adhesive over time (bottom). Error bars show standard deviation; sample size n=4.

FIG. 2 (A) is a schematic of the exemplary biocompatible adhesives (tough adhesive, "TA") of the present invention which consists of a dissipative matrix (light blue region) made of a hydrogel of hybrid ionic and covalent bonds (blue and black lines), and an adhesive surface (light green region) that contains high density primary amine polymers with positively charged primary amines (green lines). (B) and (C) are schematic views of proposed adhesion mechanisms. (D) is a schematic view of background hysteresis. (E) is a chart showing the interfacial toughness (adhesion energy) of five representative high density primary amine polymers, including polyallylamine (PAA), chitosan, polyethylenimine (PEI), collagen and gelatin. Error bars show standard deviation; sample size n=4.

FIG. 3 is a schematic of the first polymer network with covalent crosslinks (top left), the second polymer network with ionic crosslinks (top center), and the IPN including the first and second polymer networks (top right); the interfacial toughness of the first polymer network (PAAM-only), the second polymer network (alginate-only) and the IPN (PAAM/alginate) are compared (bottom). Error bars show standard deviation; sample size n=4.

FIG. 4 is a plot comparing the interfacial toughness of alginate-based IPNs of differing molecular weights. Error bars show standard deviation.

FIG. 5 (A) a schematic of spreading blood on porcine skin before applying TA; (B) is schematic and a photograph of the specimen being compressed to allow adhesion to occur; (C) is a photograph of showing some blood residue remained at the TA/Skin interface, after peeling the sample with a 180° peeling test; (D) is a schematic of the peeling test used to measure the interfacial toughness of the adhesives described herein.

Figure 10:
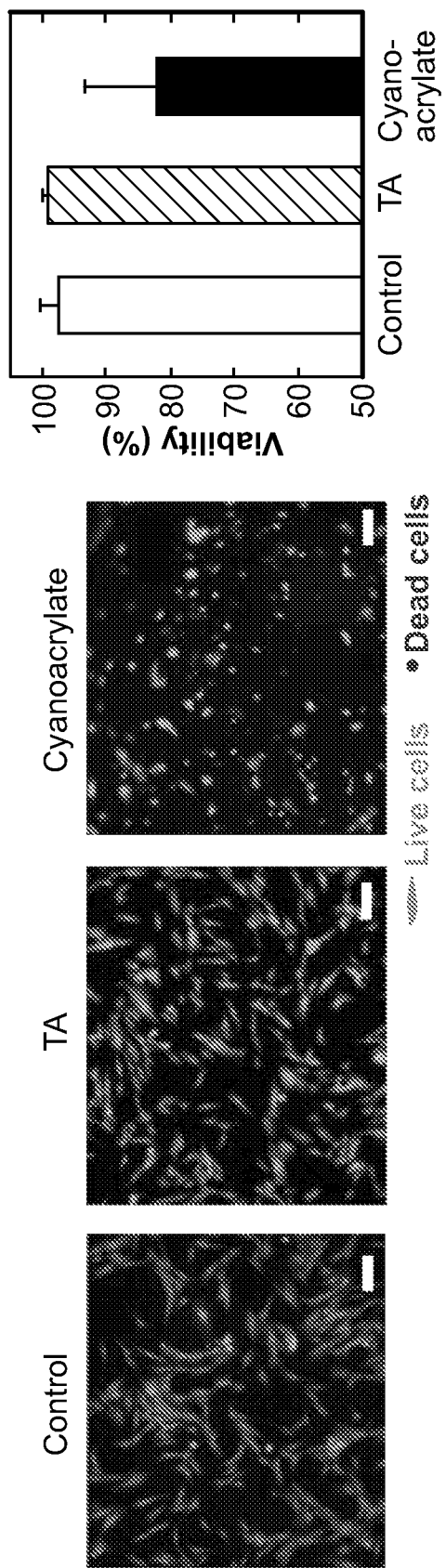

FIG. 10 is a series of photographs of an IPN hydrogel with and without the activation agent (chitosan and EDC/sulfo-NHS) soaked in cell culture media DMEM (left and center), along with cyanoacrylate (right) for comparison. Cell viability was compared between the conditions by quantifying the percentage of live cells (viability). Scalar bar, 100 µm. Error bars show standard deviation; sample size n=5.

Figure 11:
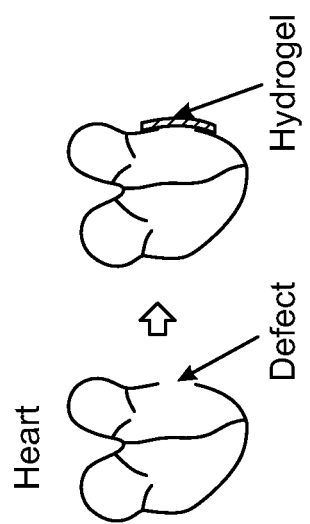

FIG. 11 is a schematic of the creation and closure of a heart defect.

Figure 12:
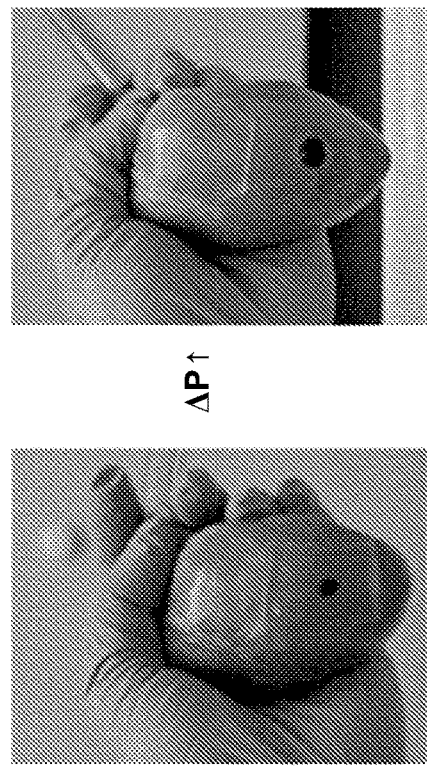
Figure 12:
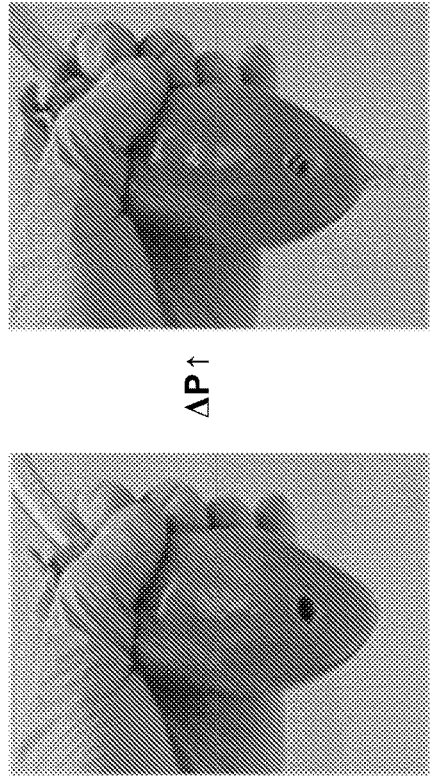
Figure 12:
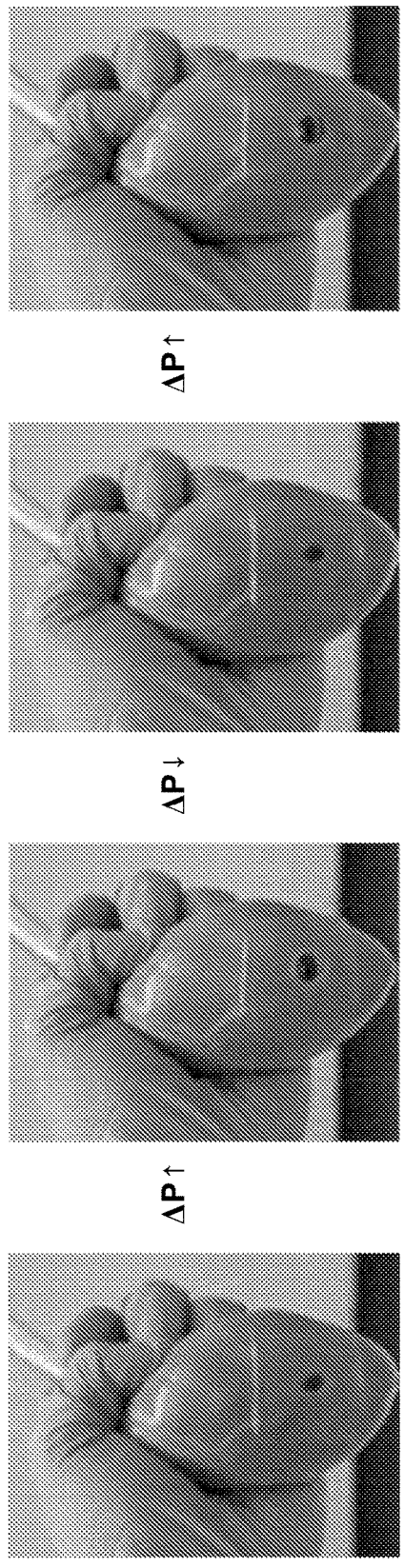

FIG. 12 is a series of photographs showing a heart with a defect without a biocompatible adhesive of the present invention applied (top) and with a biocompatible adhesive of the present invention applied (center and bottom).

Figure 13:
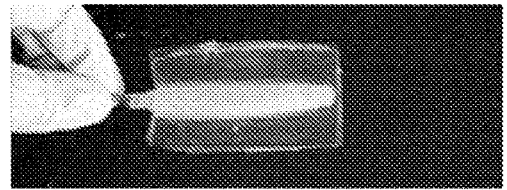
Figure 13:
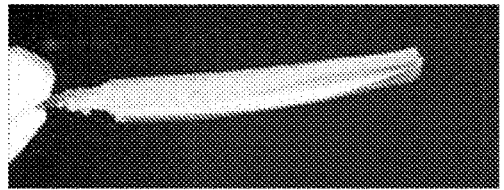
Figure 13:
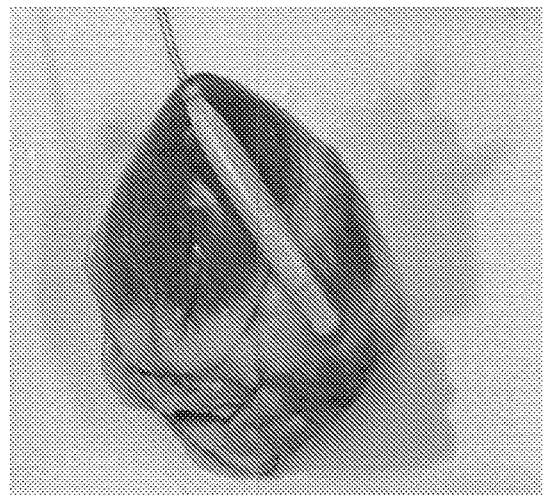
Figure 13:
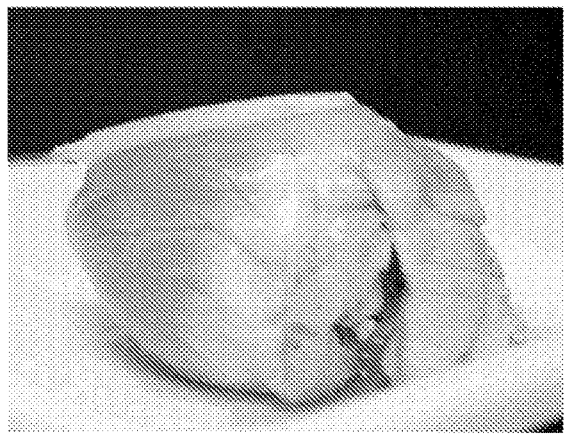
Figure 13:
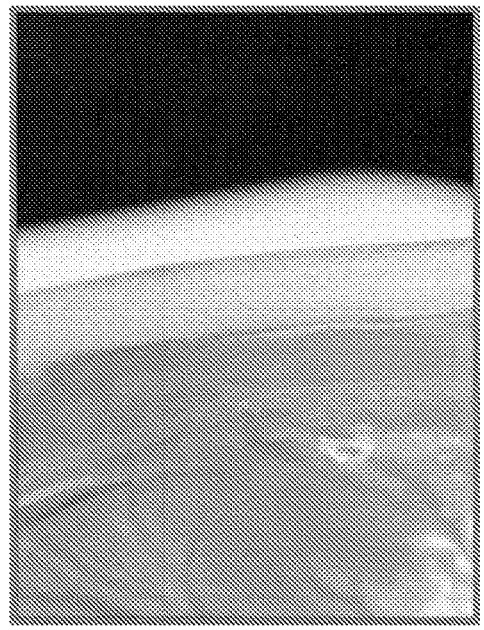

FIG. 13 is a series of photographs showing a device encapsulated with biocompatible adhesive of the present invention (top) and adhered to the surface of a heart (center and bottom).

Figure 14:
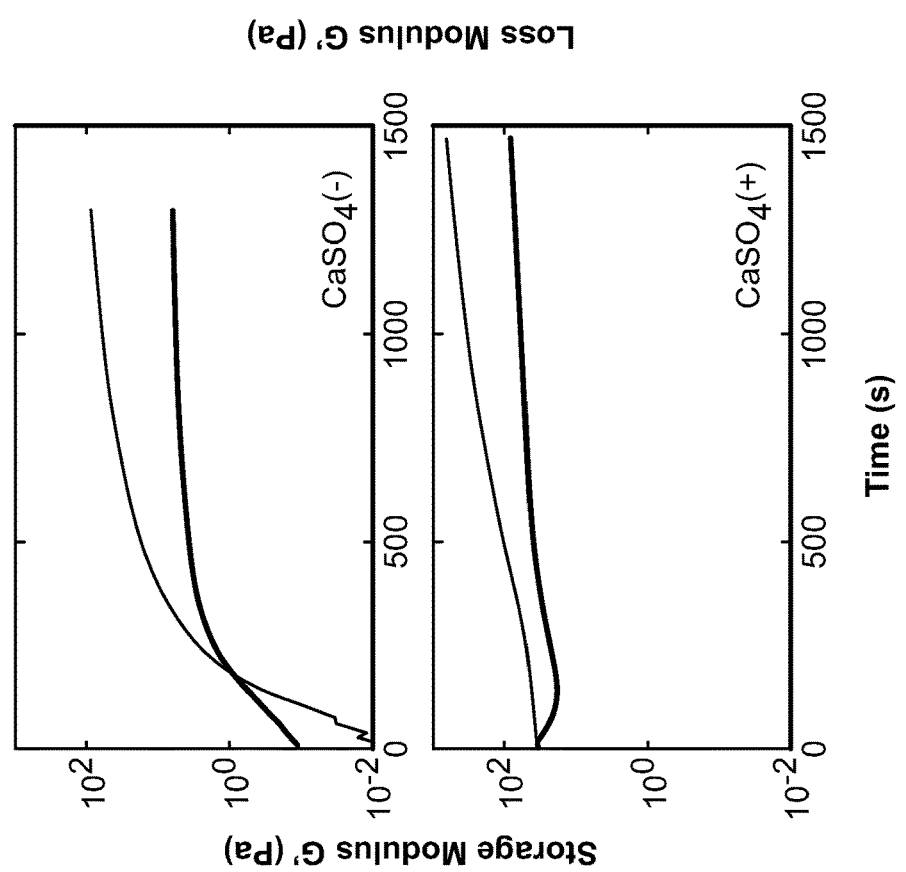

FIG. 14 are plots of the storage modulus (the top line in each plot) and loss modulus (the bottom line in each plot) of an injectable biocompatible adhesive of the present invention.

Figure 15:
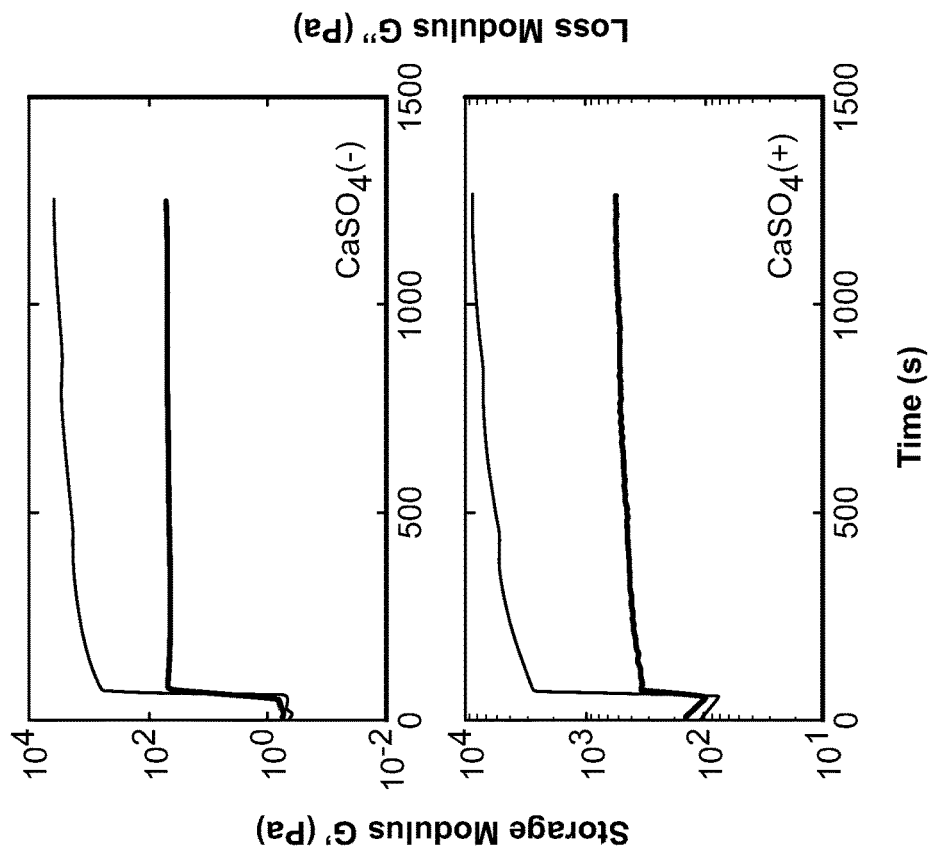

FIG. 15 are plots of the storage modulus (the top line in each plot) and loss modulus (the bottom line in each plot) of a UV-active injectable biocompatible adhesive of the present invention.

Figure 16:
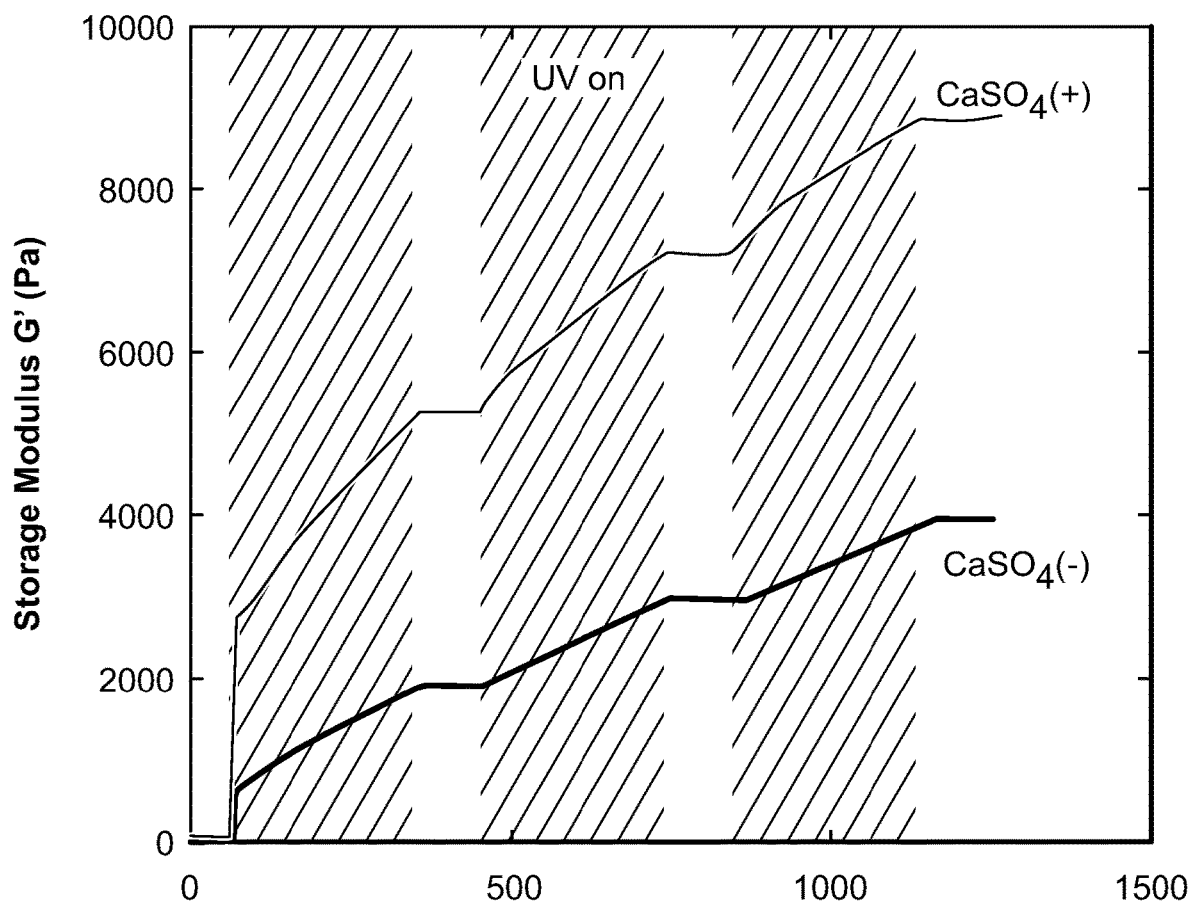

FIG. 16 is a plot of the storage modulus of UV-active injectable biocompatible adhesive of the present invention.

Figure 17:
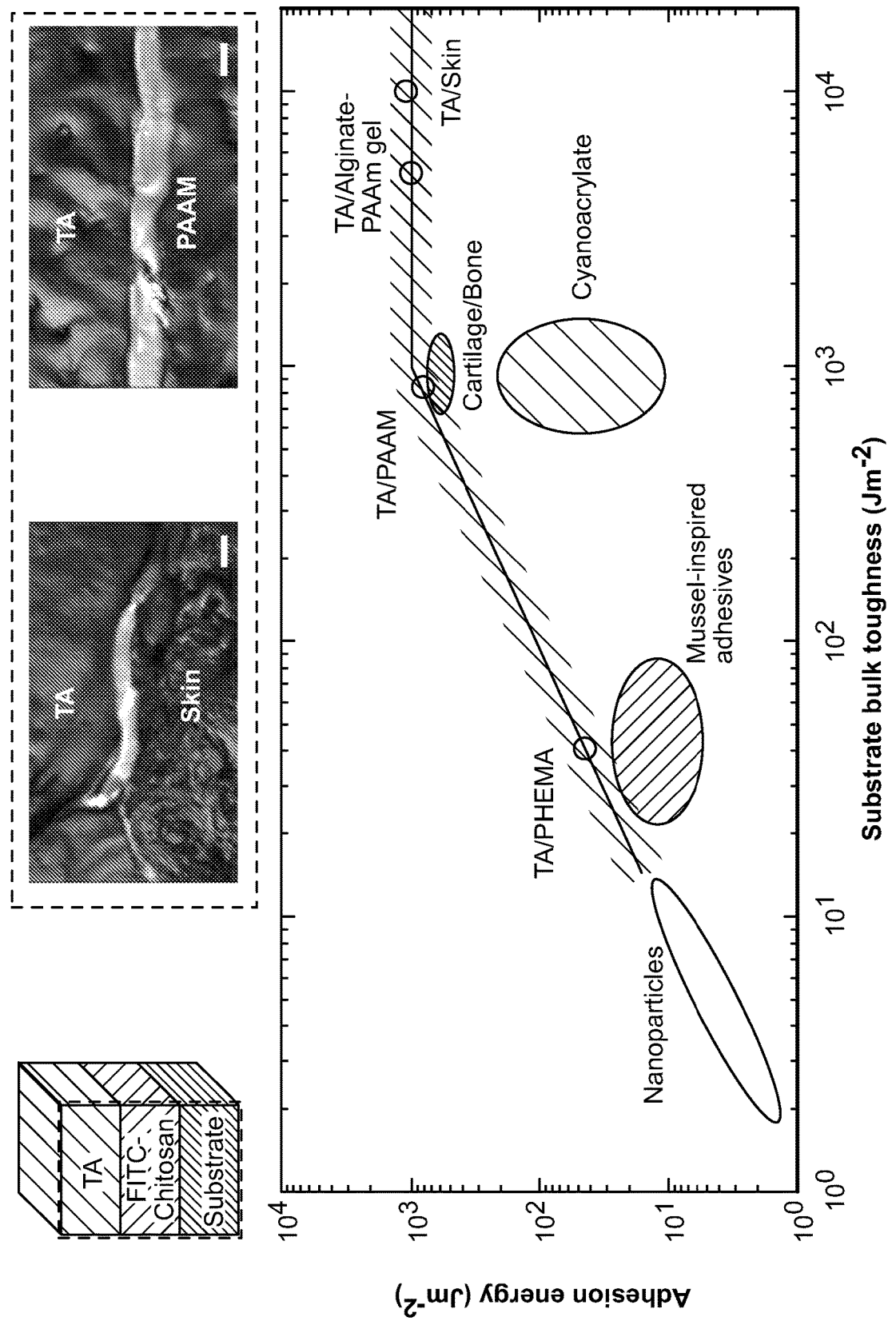

FIG. 17 is a pictorial representation and photograph of FITC-labeled chitosan showing the interfacial bridge formed by the high density primary amine polymer (i.e., chitosan) between the biocompatible adhesive ("TA", Alginate/PAAM IPN (hydrogel)/chitosan (high density primary amine polymer)/EDC/NHS (coupling agent) and the substrate, either skin (center) or a PAAM hydrogel (right), using confocal fluorescence microscopy; scalar bar, 50 µm (top); and a plot comparing the adhesion energy resulting from adhering the TA (Alginate/PAAM IPN (hydrogel)/chitosan (high density primary amine polymer)/EDC/NHS (coupling agent) on various tissues and hydrogels, plotted as a function of the bulk toughness of the substrate, along with data from the literature of nanoparticle adhesives, cyanoacrylate, mussel-inspired adhesives and the cartilage-bone joint. The tested hydrogels include a PAAM-only hydrogel, a poly (hydroxyethyl methacrylate) (PHEMA)-only hydrogel and an alginate-polyacrylamide IPN hydrogel.

Figure 18:
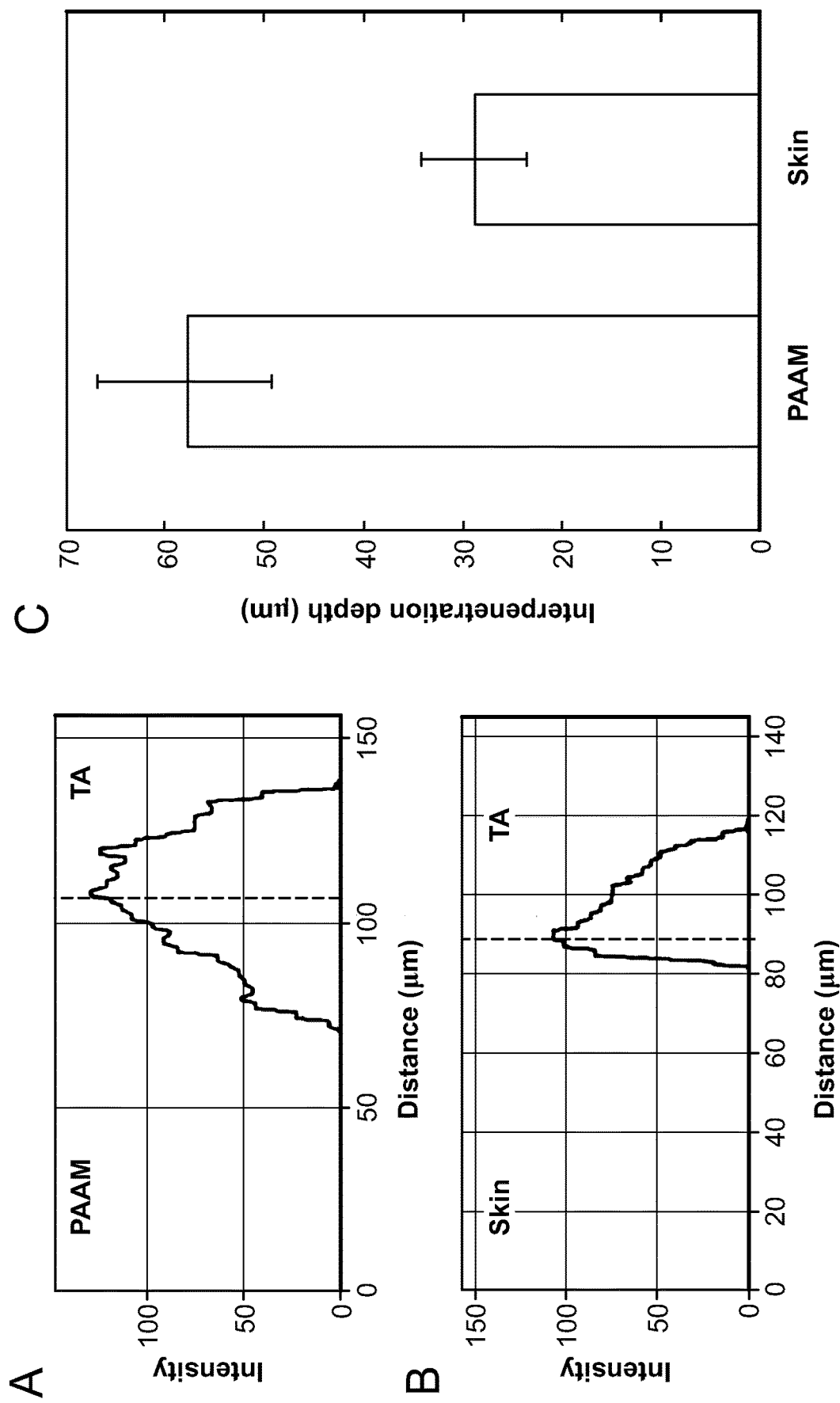

FIG. 18 is a plot showing the fluorescent intensity profile across the interface between the biocompatible adhesive and polyacrylamide hydrogel (PAAM) (A), and porcine skin (B). (C). Interpenetration depth of the FITC-labeled chitosan between TA and PAAM hydrogel, and porcine skin measured based confocal fluorescence images, error bars show standard deviation.

Figure 19:
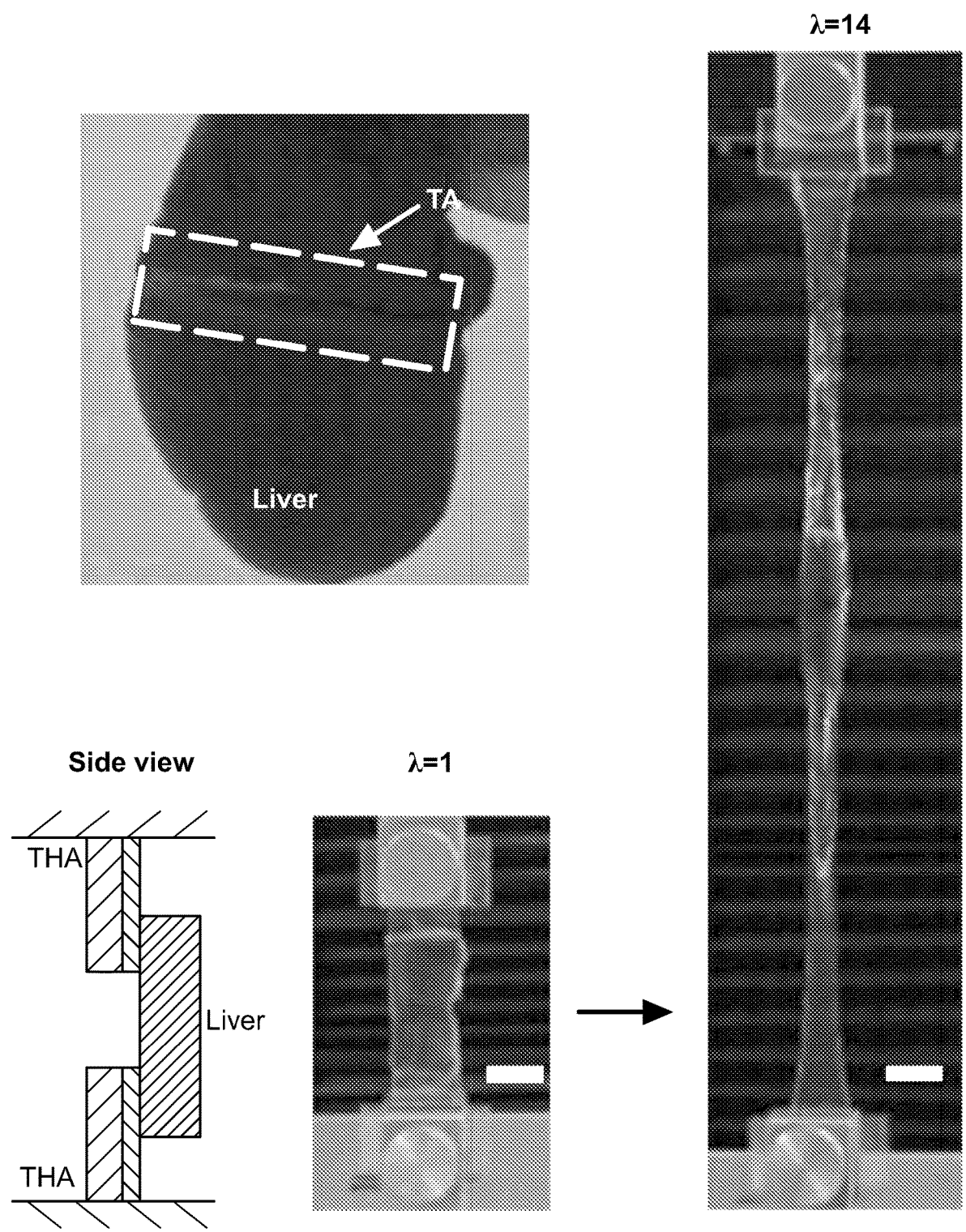

FIG. 19 are photographs showing the biocompatible adhesive (referred to as "TA") used to glue two pieces of rodent liver together. Two pieces of the biocompatible adhesive were bridged via a rodent liver, and then stretched by an Instron machine. The biocompatible adhesive adhered strongly to the liver and sustained 14 times its initial length before debonding. Scalar bar, 20 mm.

Figure 20:
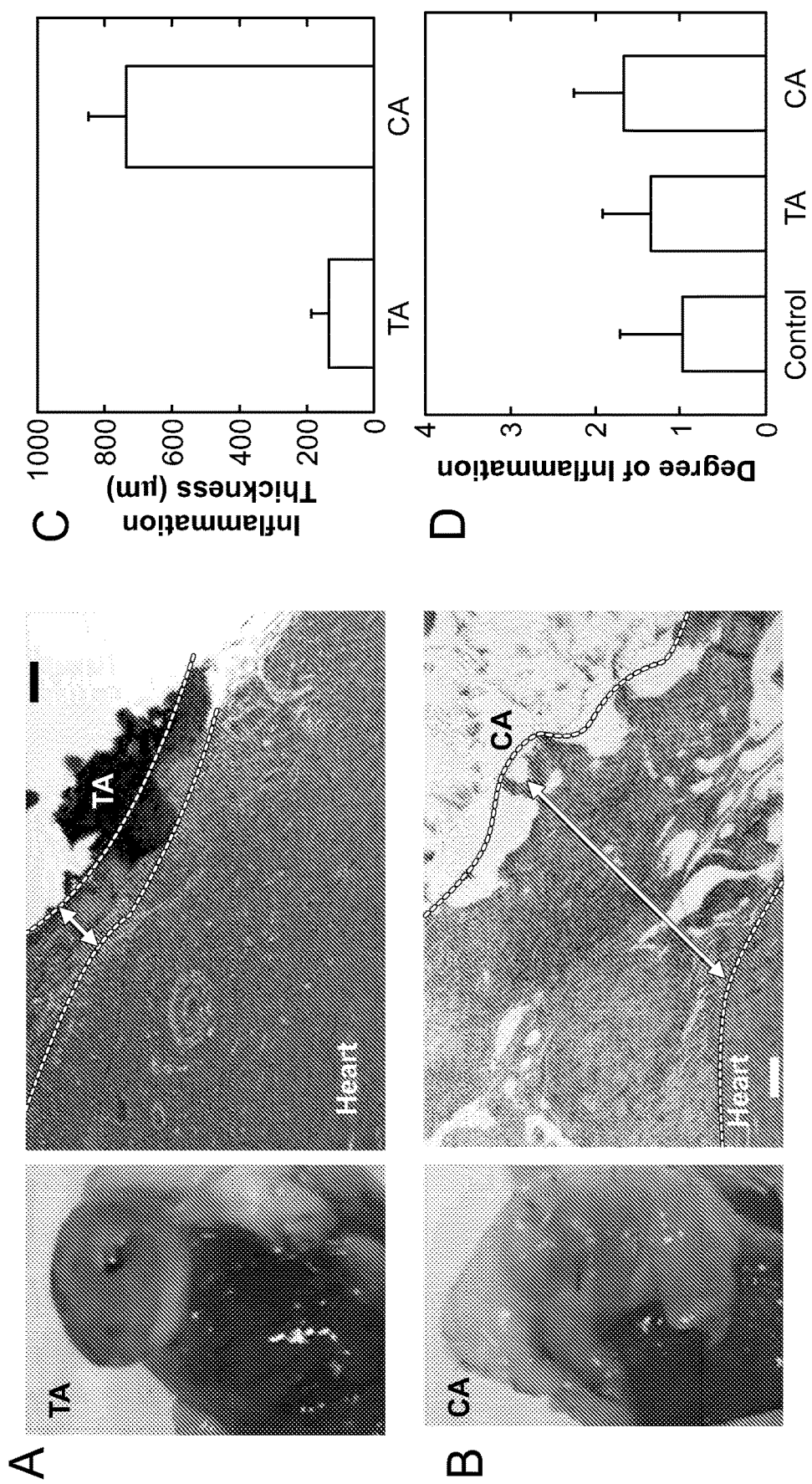

FIG. 20 is a series of photographs showing the biocompatible adhesive (referred to as "TA") displaying minimal fibrosis when attached to the rat myocardium for one week (A) and significant fibrosis on the rat myocardium elicited by cyanoacrylate (referred to as "CA") (B); scaler bar, 100 µm; and a plot of the thickness of inflammatory region measured based on histological sections (C) and a plot of the degree of inflammation was determined for all three experiments with cyanoacrylate causing the largest degree of inflammation (1=no inflammation, 2=mild, 3=moderate, 4=severe) (D). Error bars show standard deviation; sample size n=5.

Figure 21:
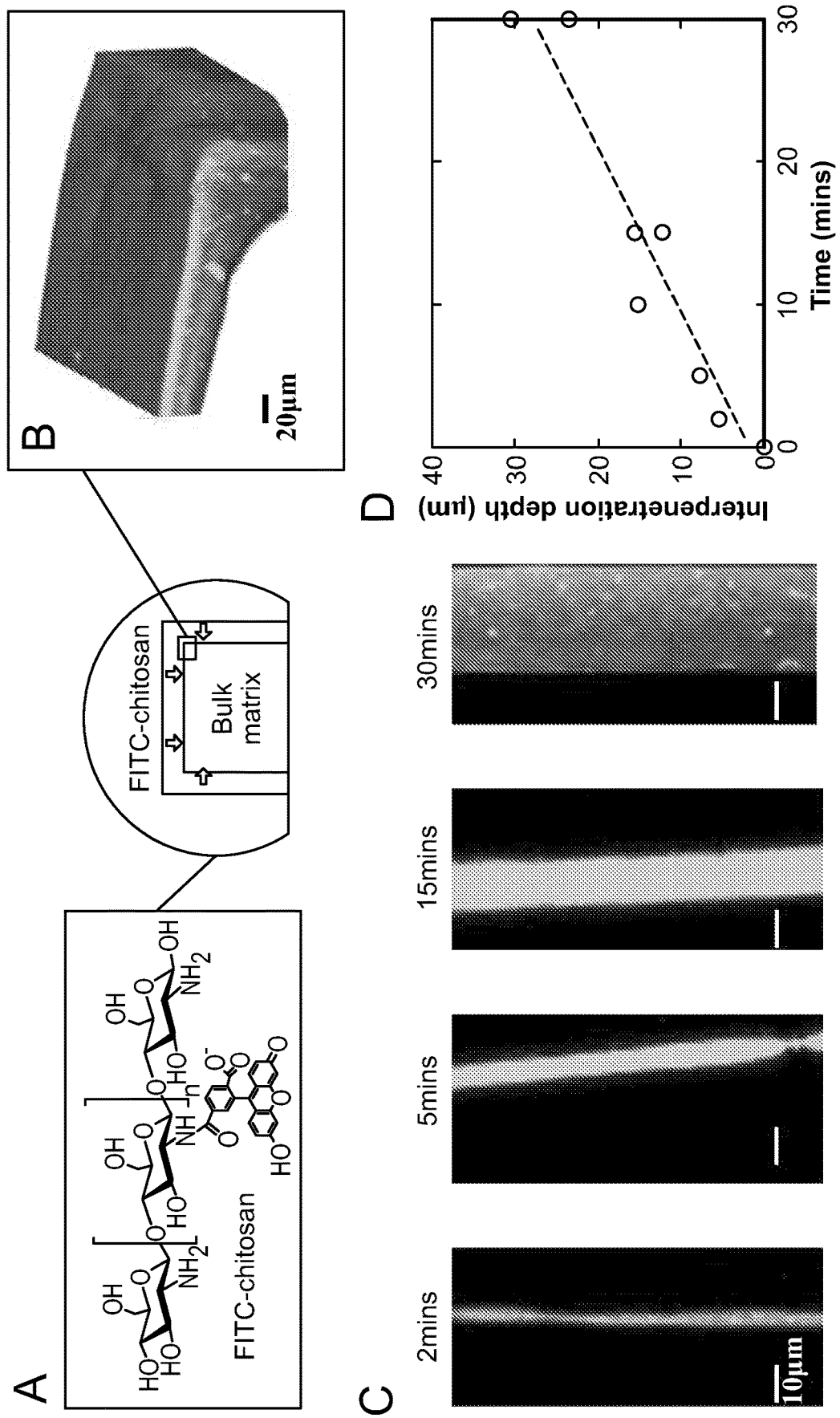

FIG. 21 (A) is a pictorial representation showing physical interpenetration of high density primary amine polymer into bulk matrix (dissipative matrix): FITC-chitosan was applied to the alginate/polyacrylamide hydrogel comprising the dissipative matrix, and allowed to diffuse into the gel; (B) are the photographs imaged by confocal fluorescence microscopy which show the diffusion of FITC-chitosan over time; (C) are images of the adhesive surface containing FITC-chitosan at different incubation times. (D) is a plot showing the depth of chitosan interpenetration increased with the incubation time.

Figure 22:
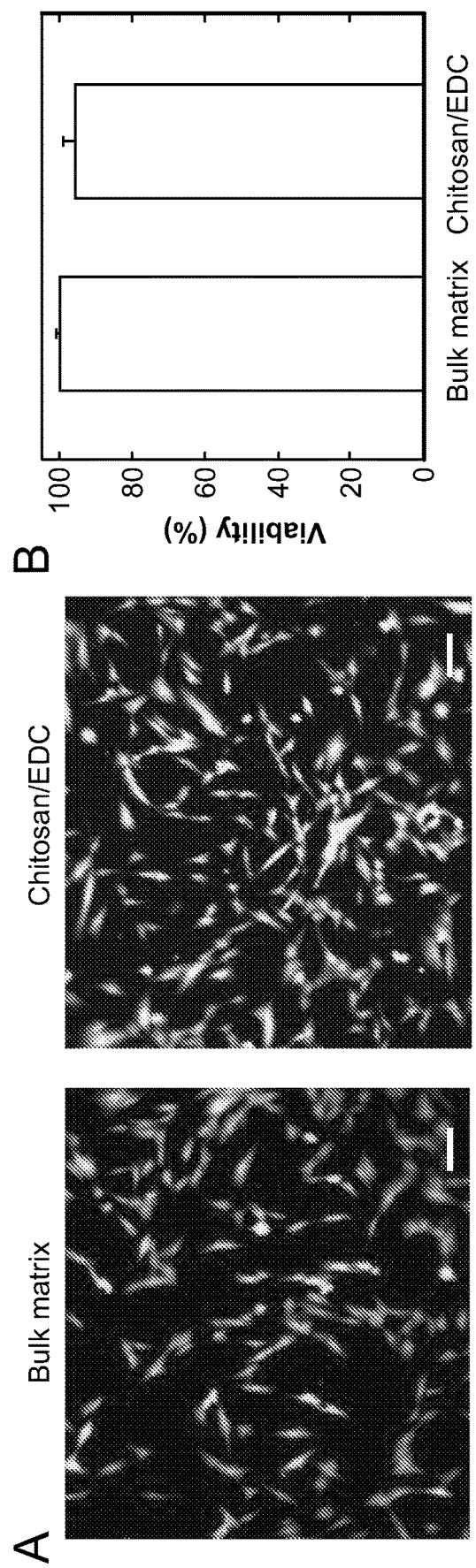

FIG. 22 (A) is a series of photographs of human dermal fibroblasts which were cultured for 24 hours in conditioned media resulting from incubating the dissipative matrix (alginate-polyacrylamide hydrogel), or the high density primary amine polymer (chitosan plus EDC) in DMEM. Live cells in green elongated form, and the dead cells in red dot form. (B) is a plot showing the cell viability comparison between the conditions by quantifying the percentage of live cells (viability). Scale bar, 100 µm. Error bars show standard deviation; sample size n=5.

Figure 23:
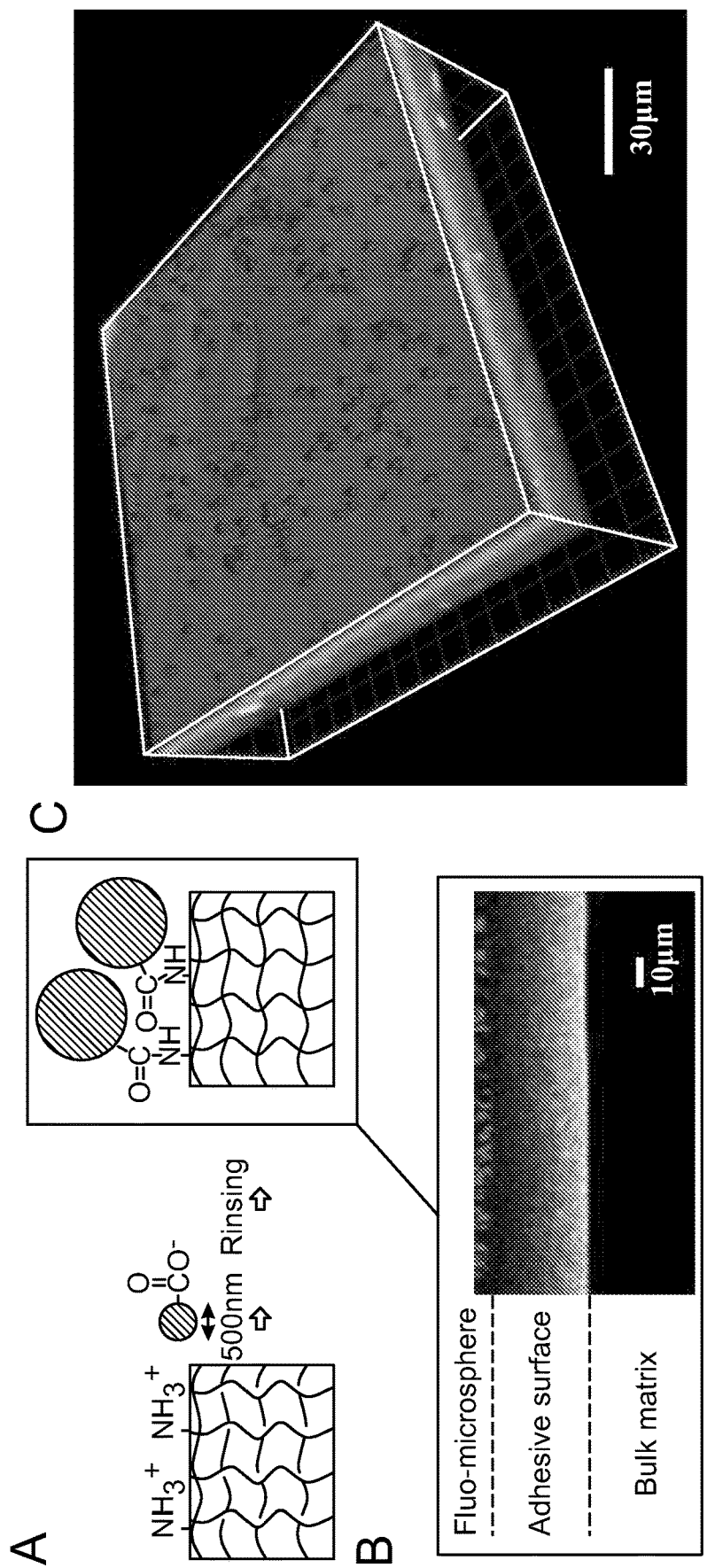

FIG. 23 (A) is a schematic showing that fluorescent microspheres of 500 nm diameter (red dots) are spread on a tough adhesive consisting of FITC-chitosan interpenetrating adhesive surface (green), and after rinsing with PBS repeatedly, the microspheres remain on the tough adhesive via electrostatic attraction and formation of amide bonds. (B) is 2D cross-section image of the sandwich structure: fluorescent microspheres (red), FITC-chitosan interpenetrating adhesive surface (green) and bulk matrix of the tough adhesive (from top to bottom). As the microphere size is larger than the mesh size of the tough adhesive (on the order of 10 nm), the microspheres remain on the outer surface. (C) is a 3D construct of fluorescent microspheres adherent to a tough adhesive.

Figure 24:
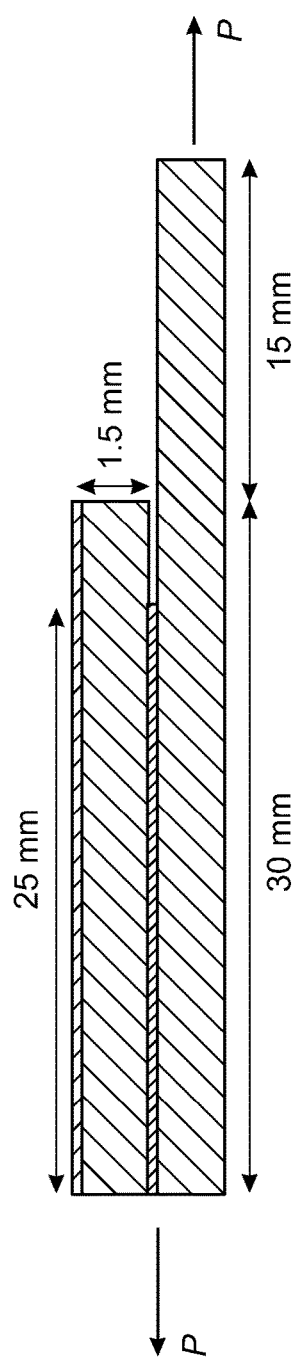
Figure 24:
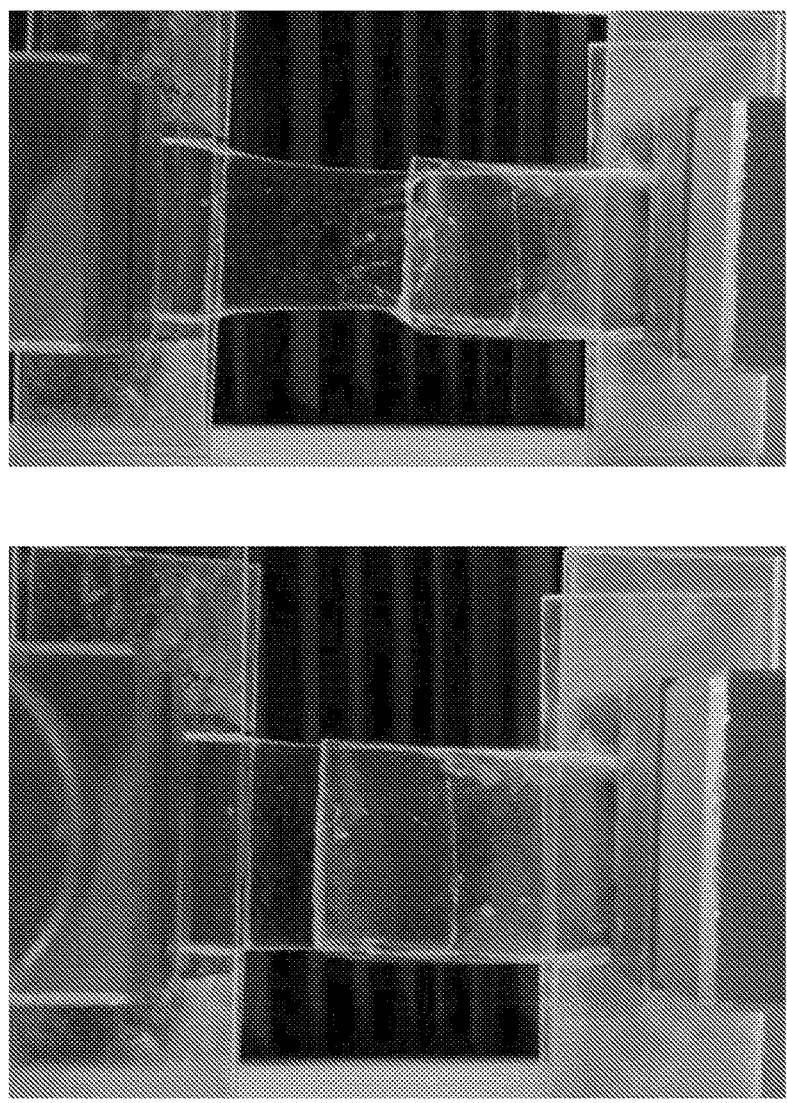

FIG. 24 is a schematic of a specimen consisting of a tough adhesive and a hydrogel with one side bonded to a polyethylene terephthalate film. The dimensions in the test are as labeled; and digital photos of a specimen before and after debonding occurs.

Figure 25:
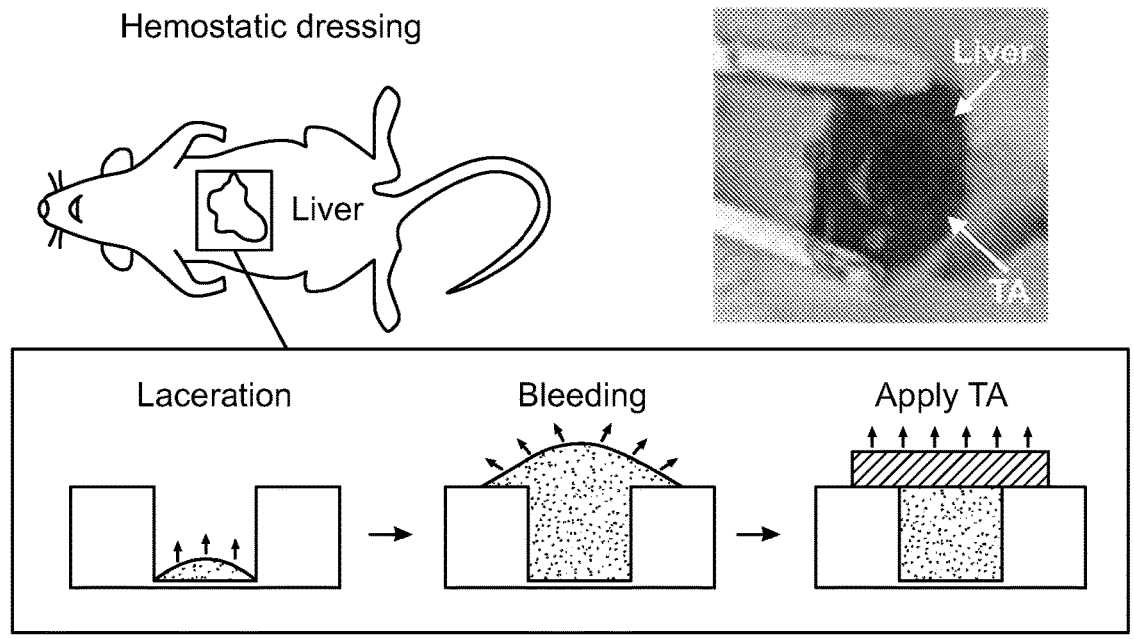
Figure 25:
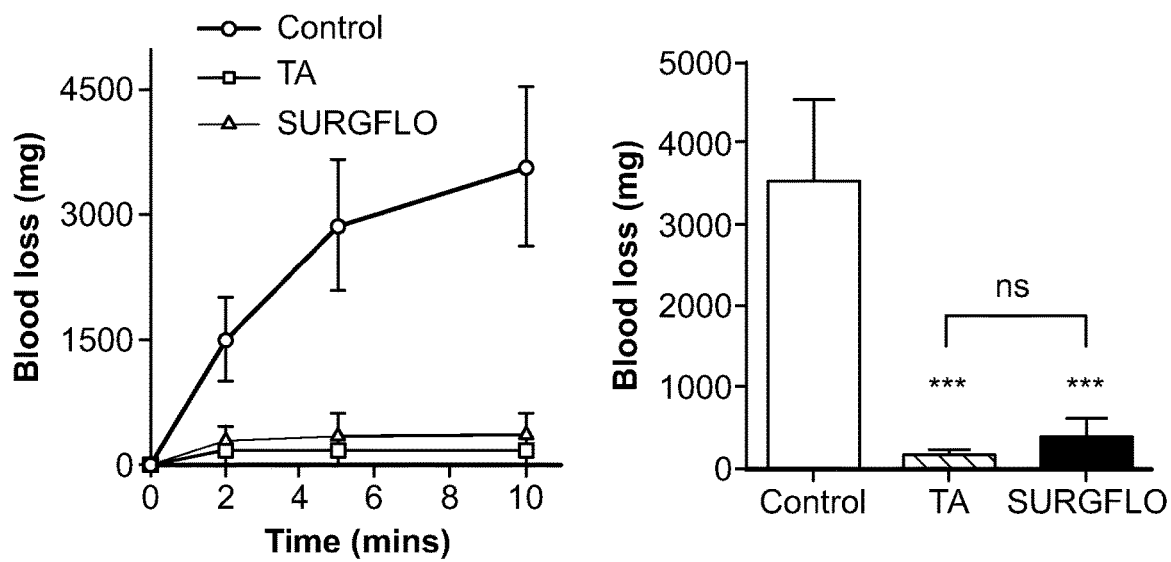

FIG. 25 is a schematic of the use of the biocompatible adhesives as a hemostatic dressing in a liver laceration model. The biocompatible adhesive is applied on the site of lesion immediately after the wound creation. The blood loss is measured as a function of time. The biocompatible adhesive reduces dramatically the blood loss similar to the SURGIFLO hemostatic matrix as compared to the negative control without any treatment.

Figure 26:
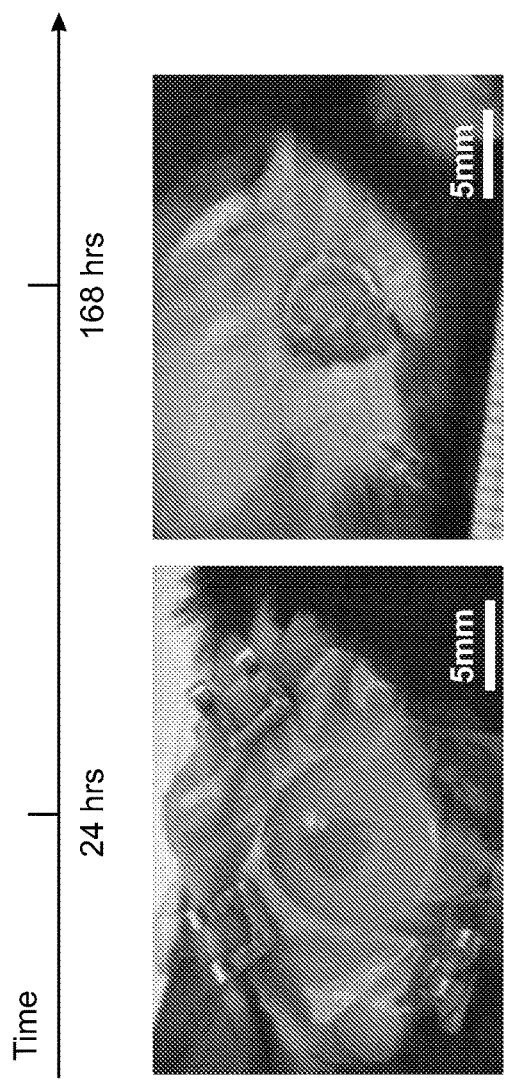
Figure 26:
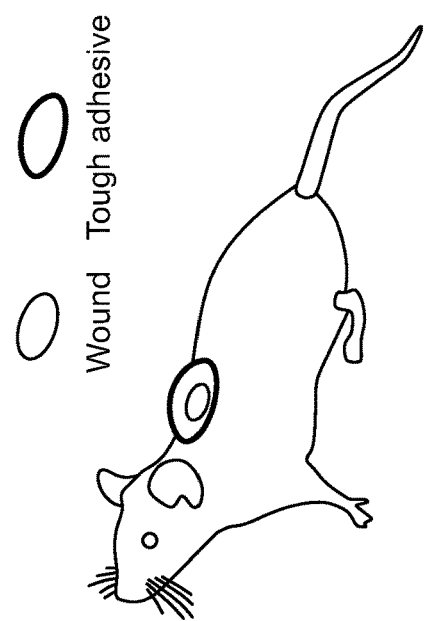

FIG. 26 is a schematic of the use of the biocompatible adhesives as a bandage for skin wound management. The biocompatible adhesive remained adherent to the skin although it dries out due to water evaporation.

Figure 27:
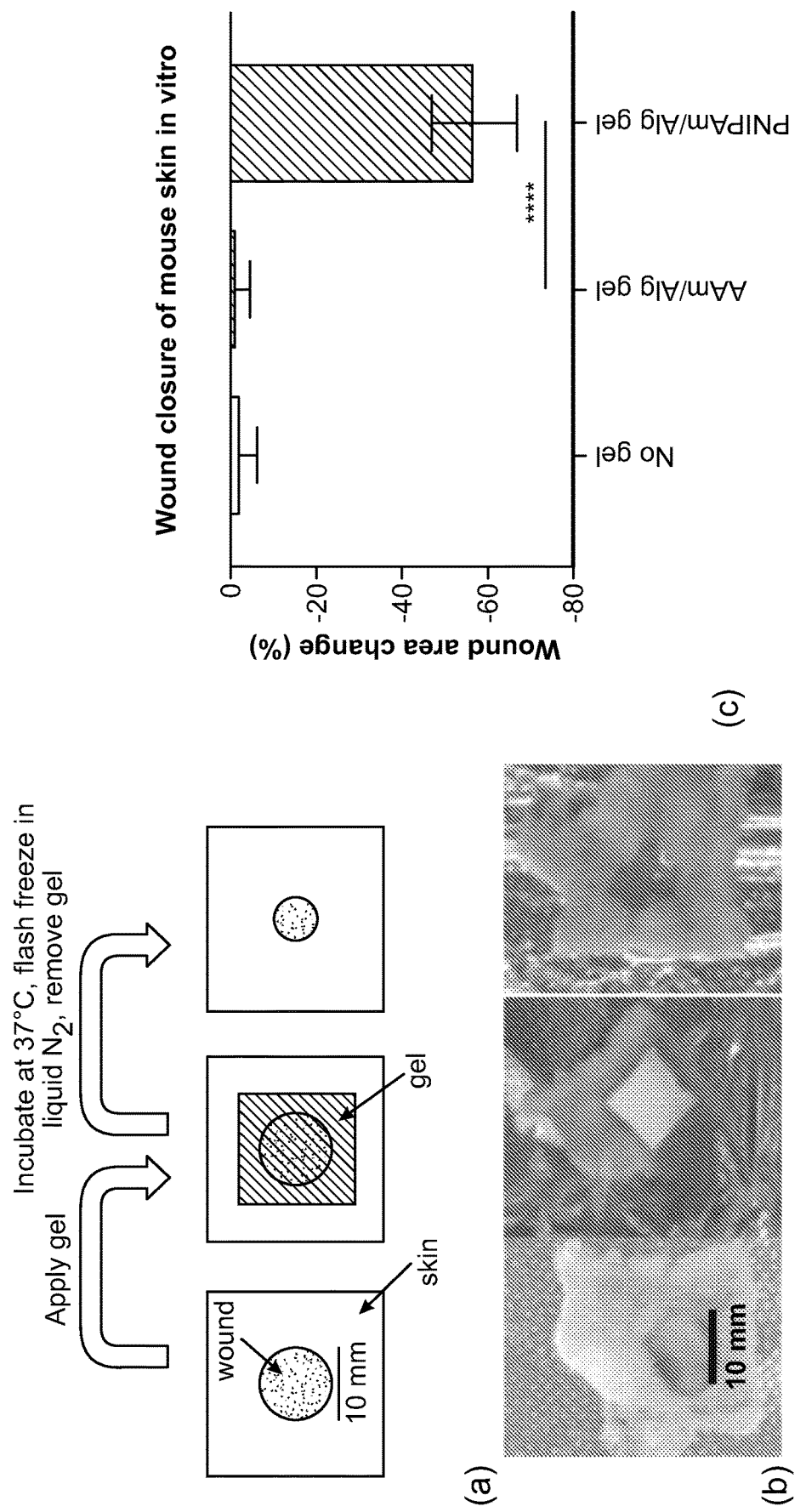

FIG. 27 is a demonstration of the use of thermo-sensitive adhesives based on PNIPAM-alginate matrix for skin wound management. This adhesive can effectively pull the wound edges together for accelerating wound closure.

Figure 28:
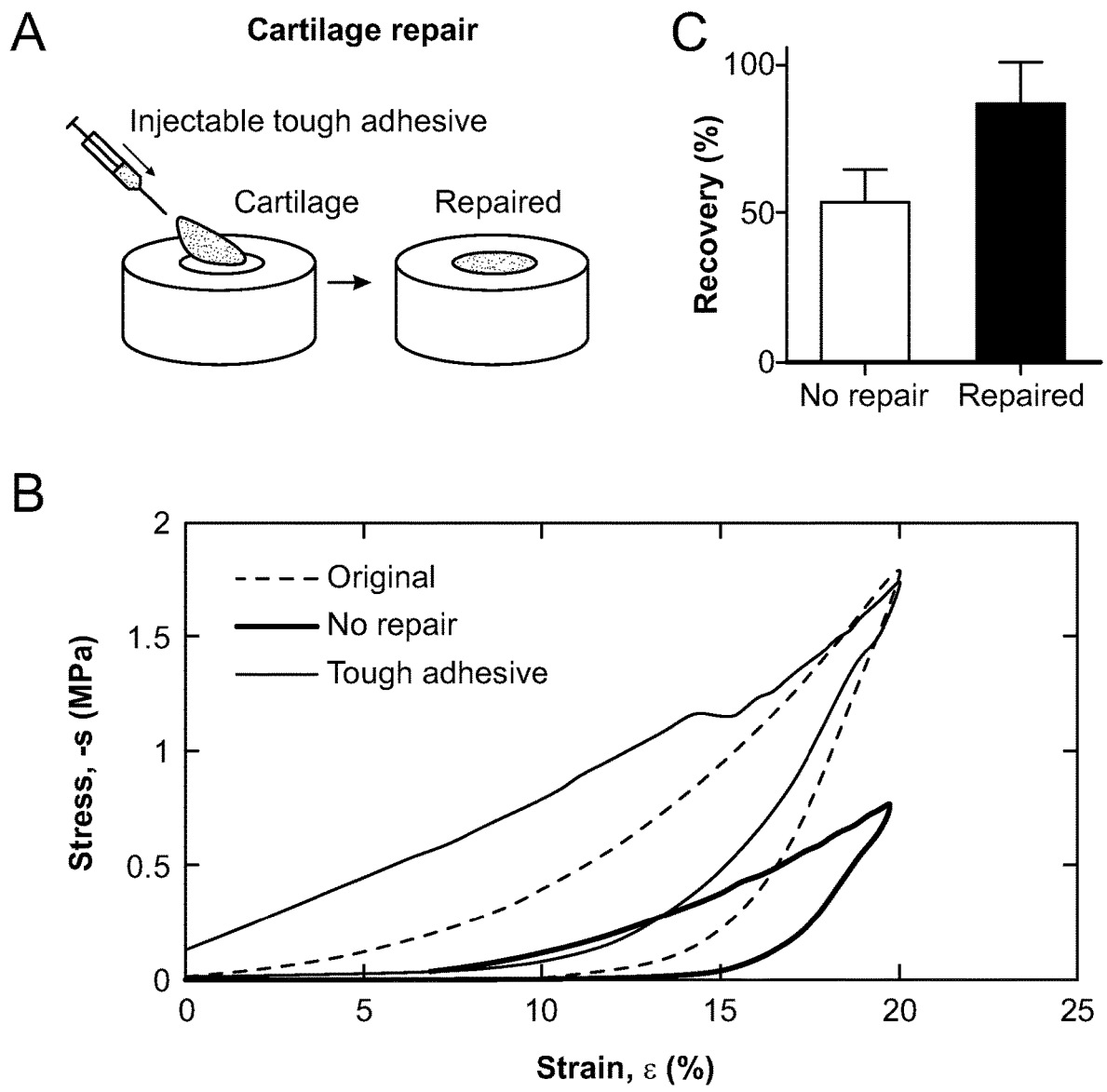

FIG. 28 is a demonstration of the use of an injectable biocompatible adhesive based on PEG and alginate, which is able to repair a defect of articular cartilage discs. The recovery is accessed with the stress level at 20% compressive strains.

Figure 29:
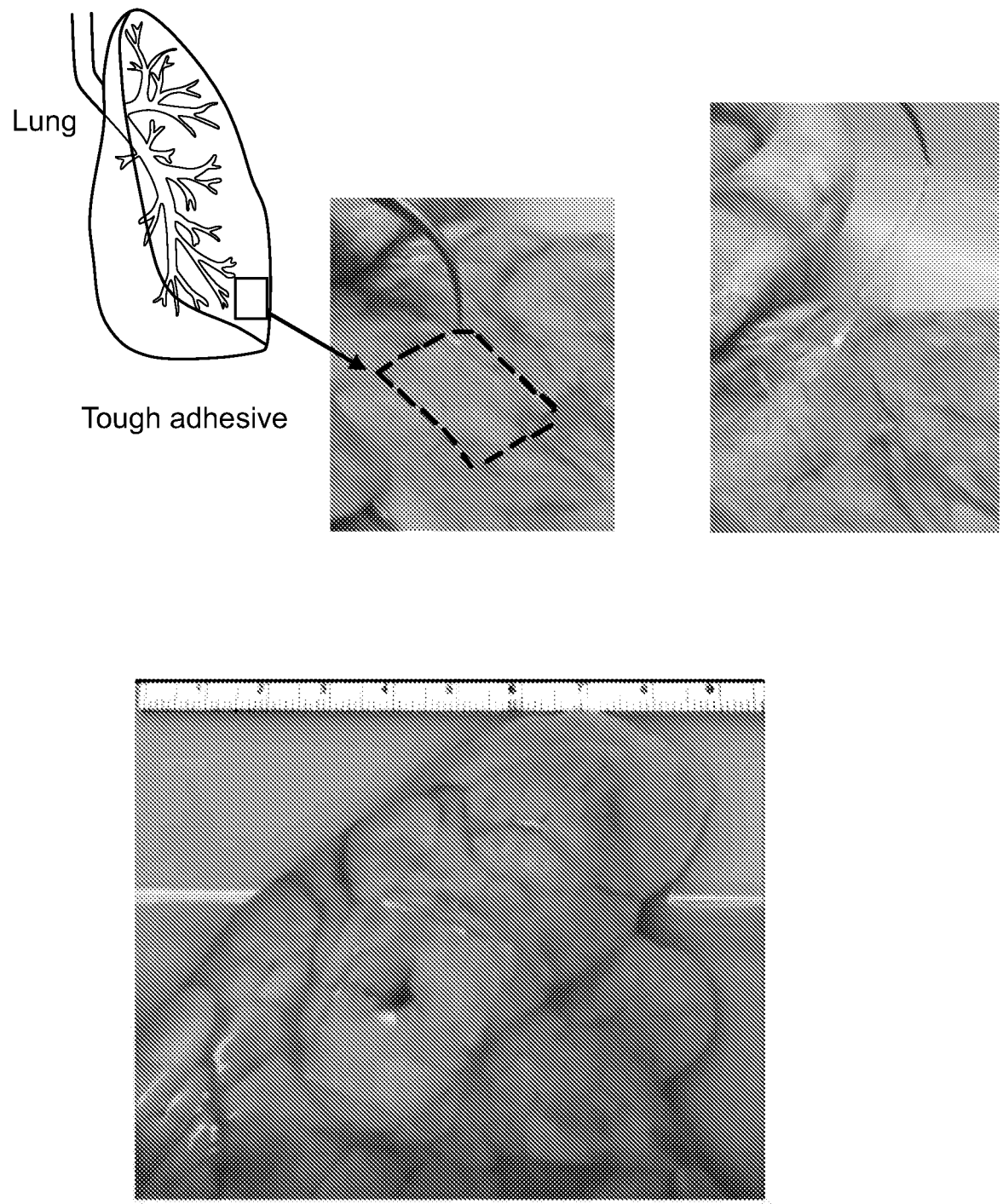

FIG. 29 shows the use of the biocompatible adhesive to attach onto a porcine lung ex vivo and to seal a lung defect.

DETAILED DESCRIPTION OF THE INVENTION

Achieving high adhesion energy requires the synergy of two effects. First, the adhesive should form strong bonds with the substrate. Second, materials inside either the adhesive or the substrate (or both) should dissipate energy by hysteresis. Adhesives for biological tissues must satisfy additional requirements, such as compatibility with blood and body fluids within the body, and biocompatibility with cells and tissues. The present invention discloses biocompatible adhesives (also referred to as tough adhesives or TA) to meet those requirements. The present invention is based, at least in part, on the discovery of biocompatible adhesives that are capable of adhering to biological surfaces (e.g., tissue or device) even in wet and dynamic environments. Accordingly, the present invention provides methods and systems for adhering a biocompatible adhesive to a biological surface (e.g., tissue or device).

The biocompatible adhesives described herein offer significant advantages, particularly in medical applications, including wound dressings, drug delivery, tissue repair, and adhesion of biomedical devices to tissues. For example, hydrogels that are used on wet, dynamic tissues, such as muscles or the heart, are subject to application of repeated stresses and strains. Since the hydrogels described herein are more mechanically robust, more durable, and are characterized by a higher interfacial toughness, they are more suitable for such applications.

I. Definitions

In order that the present invention may be more readily understood, certain terms are first defined. In addition, it should be noted that whenever a value or range of values of a parameter are recited, it is intended that values and ranges intermediate to the recited values are also part of this invention.

In the following description, for purposes of explanation, specific numbers, materials and configurations are set forth in order to provide a thorough understanding of the invention. It will be apparent, however, to one having ordinary skill in the art that the invention may be practiced without these specific details. In some instances, well-known features may be omitted or simplified so as not to obscure the present invention. Furthermore, reference in the specification to phrases such as "one embodiment" or "an embodiment" means that a particular feature, structure or characteristic described in connection with the embodiment is included in at least one embodiment of the invention. The appearances of phrases such as "in one embodiment" in various places in the specification are not necessarily all referring to the same embodiment.

The articles "a" and "an" are used herein to refer to one or to more than one (i.e., to at least one) of the grammatical object of the article. By way of example, "an element" means one element or more than one element.

As used herein the term "comprising" or "comprises" is used in reference to compositions, methods, and respective component(s) thereof, that are essential to the invention, yet open to the inclusion of unspecified elements, whether essential or not.

The term "consisting of" refers to compositions, methods, and respective components thereof as described herein, which are exclusive of any element not recited in that description of the embodiment.

By "treatment", "prevention" or "amelioration" of a disease or disorder is meant delaying or preventing the onset of such a disease or disorder, reversing, alleviating, ameliorating, inhibiting, slowing or stopping the progression, aggravation or deterioration, the progression or severity of a condition associated with such a disease or disorder, e.g., a wound or a heart defect. In one embodiment, the symptoms of a disease or disorder are alleviated by at least 5%, at least 10%, at least 20%, at least 30%, at least 40%, or at least 50%.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "patient" and "subject" are used interchangeably herein. Preferably, the subject is a mammal. The mammal can be a human, non-human primate, mouse, rat, dog, cat, horse, or cow. Mammals other than humans can be advantageously used as subjects that represent animal models of tissue or organ injuries, or other related pathologies. A subject can be male or female. The subject can be an adult, an adolescent or a child. A subject can be one who has been previously diagnosed with or identified as suffering from or having a risk for developing a tissue injury, disease or condition associated with tissue injury, or requires a device to be attached within or onto the body of the subject.

II. Systems of the Invention

The present invention provides a biocompatible adhesive system comprising a) a hydrogel comprising a first polymer network and a second polymer network, wherein the first polymer network comprises covalent crosslinks and the second polymer network comprises ionic crosslinks; b) a high density primary amine polymer; and c) a coupling agent.

In particular, a biocompatible adhesive system provides an adhesive surface to a hydrogel. As illustrated in FIG. 2A, the adhesive surface comprises interpenetrating positively charged polymers, and the hydrogel provides a bulk matrix (also referred to as a dissipative matrix) that can dissipate energy effectively under deformation. The adhesive surface can form electrostatic interactions, covalent bonds, and physical interpenetration with an adherent surface of a substrate (e.g., a tissue, a cell, or a device), while the bulk matrix dissipates energy through hysteresis under deformation. For example, for substrates that bear functional groups like amines and carboxylic acids, adhesion can be formed via electrostatic interactions and covalent bonds between the TA and the substrate (FIG. 2B). For substrates that are hydrophilic and permeable to macromolecules, the high density primary amine polymers (also referred to herein as "bridging polymers") can interpenetrate into the substrate forming physical entanglements, and also form covalent bonds with the TA matrix (FIG. 2C). When an interface is stressed, the matrix dissipates energy by breaking ionic cross-links (FIG. 2D). The combination is designated to achieve high adhesion energy and bulk toughness simultaneously.

In particular, the biocompatible adhesive system (also referred to as a Tough Adhesive (TA)) herein) includes a hydrogel that can be selectively activated with a high density primary amine polymer and an activating agent (e.g., 1-ethyl-3-(3-dimethylaminopropyl) carbodiimide (EDC) and optionally, N-hydroxysuccinimide (NHS)). Without wishing to be bound by theory, it is believed that the surface of alginate-polyacrylamide hydrogels (e.g., an alginate-based hydrogel) is activated by the high density primary amine polymer (e.g., chitosan) and a coupling agent (e.g., 1-ethyl-3-(3-dimethylaminopropyl) carbodiimide (EDC)). In particular, the positive charges on the high density primary amine polymer balance the negative charges on the hydrogel, while the coupling agent catalyzes formation of amide bonds between the high density primary amine polymer and the hydrogel. Meanwhile, the activated surface allows the high density primary amine polymer and coupling agent to form chemical bonds to bridge the interface between the hydrogel and the surface of a substrate (e.g., a tissue, a cell, or a device).

As used herein, the term "contacting" (e.g., contacting a surface) is intended to include any form of interaction (e.g., direct or indirect interaction) of a hydrogel and a surface (e.g., tissue or device). Contacting a surface with a composition may be performed either in vivo or in vitro. In certain embodiments, the surface is contacted with the biocompatible adhesive in vitro and subsequently transferred into a subject in an ex vivo method of administration. Contacting the surface with the biocompatible adhesive in vivo may be done, for example, by injecting the biocompatible adhesive into the surface, or by injecting the biocompatible adhesive into or around the surface.

In some embodiments, the hydrogel used in the biocompatible adhesive of the invention is an interpenetrating network (IPN) hydrogel. As used herein, an IPN is a polymer comprising two or more networks (e.g., the first polymer network and the second polymer network) which are at least partially interlaced on a molecular scale but not covalently bonded to each other and cannot be separated unless chemical bonds are broken. IPN hydrogels are made by combining covalently crosslinked and ionically crosslinked polymer networks. Alternatively, the first polymer network and the second polymer network are covalently coupled.

The hydrogels as used in the present invention are capable of dissipating energy. For example, alginate-polyacrylamide hydrogels, as an example, possess ionic cross-links formed via electrostatic interactions between alginate and calcium ions that can break and dissipate energy under deformation.

In particular, the first polymer network comprises covalent crosslinks and includes a polymer selected from the group consisting of polyacrylamide (PAAM), poly(hydroxyethylmethacrylate) (PHEMA), poly(vinyl alcohol) (PVA), polyethylene glycol (PEG), polyphosphazene, collagen, gelatin, poly(acrylate), poly(methacrylate), poly(methacrylamide), poly(acrylic acid), poly(N-isopropylacrylamide) (PNIPAM), poly(N,N-dimentylacrylamide), poly(allylamine) and copolymers thereof. In a particular embodiment, the first polymer network is polyethylene glycol (PEG). In some embodiments, the first polymer network is polyacrylamide (PAAM).

The second polymer network includes ionic crosslinks and is a polymer selected from the group consisting of alginate (alginic acid or align), pectate (pectinic acid or polygalacturonic acid), carboxymethyl cellulose (CMC or cellulose gum), hyaluronate (hyaluronic acid or hyaluronan), chitosan, κ-carrageenan, ι-carrageenan and λ-carrageenan, wherein the wherein the alginate, carboxymethyl cellulose, hyaluronate, chitosan, κ-carrageenan, ι-carrageenan and λ-carrageenan are each optionally oxidized, wherein the alginate, hyaluronate, chitosan, κ-carrageenan, ι-carrageenan and λ-carrageenan optionally include one or more groups selected from the group consisting of methacrylate, acrylate, acrylamide, methacrylamide, thiol, hydrazine, tetrazine, norbornene, transcyclooctene and cyclooctyne.

In a particular embodiment, the second polymer network is alginate, which is comprised of (1-4)-linked b-D-mannuronic acid (M) and a-L-guluronic acid (G) monomers that vary in amount and sequential distribution along the polymer chain. Alginate is also considered a block copolymer, composed of sequential M units (M blocks), regions of sequential G units (G blocks), and regions of alternating M and G units (M-G blocks) that provide the molecule with its unique properties. Alginates have the ability to bind divalent cations such as $Ca^{+2}$ between the G blocks of adjacent alginate chains, creating ionic interchain bridges between flexible regions of M blocks. In some embodiments, the alginate is a mixture of a high molecular weight alginate and a low molecular weight alginate. For example, the ratio of the high molecular weight alginate to the low molecular weight alginate is about 5:1 to about 1:5; about 4:1 to about 1:4; about 3:1 to about 1:3; about 2:1 to about 1:2; or about 1:1. The high molecular weight alginate has a molecular weight from about 100 kDa to about 300 kDa, from about 150 kDa to about 250 kDa, or is about 200 kDa. The low molecular weight alginate has a molecular weight from about 1 kDa to about 100 kDa, from about 5 kDa to about 50 kDa, from about 10 kDa to about 30 kDa, or is about 20 kDa.

The hydrogels of the invention are highly absorbent and comprise about 30% to about 98% water (e.g., about 40%, about, about 50%, about 60%, about 70%, about 80%, about 90%, about 95%, about 98%, about 40 to about 98%, about 50 to about 98%, about 60 to about 98%, about 70 to about 98%, about 80 to about 98%, about 90 to about 98%, or about 95 to about 98% water) and possess a degree of flexibility similar to natural tissue, due to their significant water content. In particular, the hydrogels of the present invention can be stretched up to 20 times their initial length, e.g., the hydrogels of present invention can be stretched from 2 to 20 times their initial length, 5 to 20 times their initial length, 10 to 20 times their initial length, from 15 to 20 times their initial length, from 2 to 10 times their initial length, from 10 to 15 times their initial length, and from 5 to 15 times their initial length without cracking or tearing.

In some embodiment, the hydrogel is fabricated in the form of a patch. The patch can either be preformed and ready to be applied to a surface or the patch can be cut to the desired size and shape prior to application.

Alternatively, in some embodiment, the biocompatible systems of the present invention may be delivered by injection. Water soluble sodium alginate readily binds calcium, forming an insoluble calcium alginate hydrocolloid (Sutherland, 1991, *Biomaterials*, Palgrave Macmillan UK:307-331). These gentle gelling conditions have made alginate a popular material as an injectable cell delivery vehicle (Atala et al., 1994, *J. Urol.* 152(2 Pt 2):641-3). Accordingly, in some embodiments, the biocompatible adhesive is suitable for injection into a subject. Injectable adhesives may include a polymer that includes at least two reactive moieties that react and form the first polymer network upon injection. The two reactive moieties may be present on each polymer or the polymer is made of two populations of polymers, each one with a different reactive moiety. Exemplary reactive moieties include methacrylate, acrylate, acrylamide, methacrylamide, thiol, hydrazine, tetrazine, norbornene, transcyclooctene and cyclooctyne. In a particular embodiment, a PEG-based polymer is prepared by reacting a PEG containing a norborne functional group and a PEG containing a tetrazine functional group to form the first polymer network. In a particular embodiment, the two reactive moieties react in the presence of UV light. In a particular embodiment, the two reactive moieties react in the presence of $Ca^{2+}$ (e.g., $CaSO_4$).

The biocompatible adhesive includes a high density primary amine polymer (also referred to herein as a "bridging polymer." The high density primary amine polymer forms covalent bonds with both the hydrogel and the surface, bridging the two. The high density primary amine polymer bears positively charged primary amine groups under physiological conditions. In some embodiments, the high density primary amine polymer can be absorbed to a surface (e.g., a tissue, a cell, or a device) via electrostatic interactions, and provide primary amine groups to bind covalently with both carboxylic acid groups in the hydrogel and on the surface. If the surface is permeable, the high density primary amine polymer can also penetrate into the surface, forming physical entanglements, and then chemically anchor the hydrogel As used herein, the high density primary amine polymer includes at least one primary amine per monomer unit. In some embodiments, the high density primary amine polymer is selected from the group consisting of chitosan, gelatin, collagen, polyallylamine, polylysine, and polyethylenimine. In particular, polyallylamine (PolyNH$_2$ or PAA) is represented by the following structural formula:

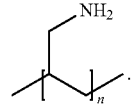

In particular, chitosan is represented by the following structural formula:

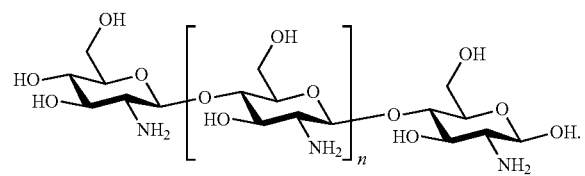

In particular, polyethylenimine (PEI) is represented by the following structural formula:

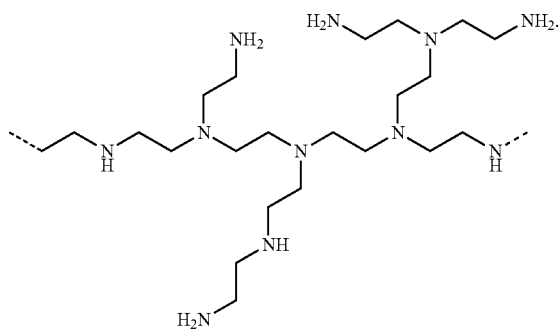

In particular, polylysine is represented by the following structural formula:

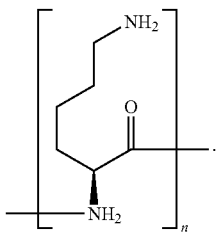

Collagen and/or gelatin include approximately ~10% amino acid with primary amine (e.g., Arg, Lysine). A comparison of the interfacial toughness of the exemplary high density primary amine polymers is described in Example 3 and FIG. 2(E).

The biocompatible adhesive also includes a coupling agent. As used herein, the coupling agent activates one or more of the primary amines present in the high density primary amine polymer. Once activated with the coupling agent, the primary amine forms an amide bond with the hydrogel and the target surface (e.g., a tissue, an organ, or a medical device). In some embodiments, the coupling agent includes a first carboxyl activating agent, wherein the first carboxyl activating agent is a carbodiimide. Exemplary carbodiimides are selected from the group consisting of 1-ethyl-3-(3-dimethylaminopropyl)carbodiimide (EDC, EDAC or EDCI), dicyclohexylcarbodiimide (DCC) and diisopropylcarbodiimide (DIC). In some embodiments, the first carboxyl activating agent is EDC.

In some embodiments, the coupling agent further includes a second carboxyl activating agent. Exemplary second carboxyl activating agents include, but are not limited to, N-hydroxysuccinimide (NHS), N-hydroxysulfosuccinimide (sulfo-NHS), hydroxybenzotriazole (HOBt), dimethylaminopyridine (DMAP), Hydroxy-3,4-dihydro-4-oxo-1,2,3-benzotriazine (HOOBt/HODhbt), 1-Hydroxy-7-aza-1H-benzotriazole (HOAt), Ethyl 2-cyano-2-(hydroximino) acetate, Benzotriazol-1-yloxy-tris(dimethylamino)-phosphonium hexafluorophosphate (BOP), Benzotriazol-1-yloxy-tripyrrolidino-phosphonium hexafluorophosphate, 7-Aza-benzotriazol-1-yloxy-tripyrrolidinophosphonium hexafluorophosphate), Ethyl cyano(hydroxyimino)acetato-O2)-tri-(1-pyrrolidinyl)-phosphonium hexafluorophosphate, 3-(Diethoxy-phosphoryloxy)-1,2,3-benzo[d] triazin-4(3H)-one, 2-(1H-Benzotriazol-1-yl)-N,N,N',N'-tetramethylaminium tetrafluoroborate/hexafluorophosphate, 2-(6-Chloro-1H-benzotriazol-1-yl)-N,N,N',N'-tetramethylaminium hexafluorophosphate), N-[(5-Chloro-1H-benzotriazol-1-yl)-dimethylamino-morpholino]-uronium hexafluorophosphate N-oxide, 2-(7-Aza-1H-benzotriazol-1-yl)-N,N,N',N'-tetramethylaminium hexafluorophosphate, 1-[1-(Cyano-2-ethoxy-2-oxoethylideneaminooxy)-dimethylamino-morpholine]-uronium hexafluorophosphate, 2-(1-Oxy-pyridin-2-yl)-1,1,3,3-tetramethylisothiouronium tetrafluoroborate, Tetramethylfluoroformamidinium hexafluorophosphate, N-Ethoxycarbonyl-2-ethoxy-1,2-dihydroquinoline, 2-Propanephosphonic acid anhydride, 4-(4,6-Dimethoxy-1,3,5-triazin-2-yl)-4-methylmorpholinium salts, (bis-Trichloromethylcarbonate, 1,1'-Carbonyldiimidazole. In some embodiments, the first carboxyl activating agent is NHS.

In some embodiments, the high density primary amine polymer and the coupling agent are packaged separately.

In some embodiments, the high density primary amine polymer is in a solution and the coupling agent is in solid form. In a particular, the coupling agent is added to the high density primary amine polymer solution. In some embodiments, the high density primary amine polymer is in a solution, the coupling agent is added to the high density primary amine polymer solution, and the solution is applied to the hydrogel.

In some embodiments, the concentration of the high density primary amine polymer in the solution is about 0.1% to about 50%, for example, from about 0.2% to about 40%, about 0.5% to about 30%, about 1.0% to about 20%, about 1% to about 10%, about 0.2% to about 10%, about 10% to about 20%, about 20% to about 30%, or about 40% to about 50%. In some embodiments, the coupling agent includes at least a first carboxyl activating agent and optionally a second carboxyl activating agent, and wherein the concentration of the first carboxyl activating agent in the solution is about 3 mg/mL to about 50 mg/mL, for example from about 5 mg/mL to about 40 mg/mL, about 7 mg/mL to about 30 mg/mL, about 9 mg/mL to about 20 mg/mL, about 3 mg/mL to about 45 mg/mL, 3 mg/mL to about 40 mg/mL, 3 mg/mL to about 35 mg/mL, about 3 mg/mL to about 30 mg/mL, 3 mg/mL to about 25 mg/mL, about 3 mg/mL to about 20 mg/mL, 3 mg/mL to about 15 mg/mL, about 3 mg/mL to about 10 mg/mL, about 5 mg/mL to about 50 mg/mL, about 10 mg/mL to about 50 mg/mL, about 15 mg/mL to about 50 mg/mL, about 20 mg/mL to about 50 mg/mL, about 25 mg/mL to about 50 mg/mL, about 30 mg/mL to about 50 mg/mL, about 35 mg/mL to about 50 mg/mL, about 40 mg/mL to about 50 mg/mL, or about 3 mg/mL to about 45 mg/mL.

In some embodiments, the system includes a first therapeutically active agent. The first therapeutically active agent may be encapsulated in or attached to the surface of the hydrogel. Alternatively, the first therapeutically active agent is encapsulated in or attached to the surface of the high density primary amine polymer. In certain embodiments, the system further comprises a second therapeutically active agent. The second therapeutically active agent is encapsulated in or attached to the surface of the hydrogel. Alternatively, the second therapeutically active agent is encapsulated in or attached to the surface of the high density primary amine polymer. The first and second therapeutically active agents are independently selected from the group consisting of a small molecule, a biologic, a nanoparticle, and a cell. The biologic is selected from the group consisting of a growth factor, an antibody, a vaccine, a cytokine, a chemokine, a hormone, a protein, and a nucleic acid. The amount of therapeutically active agents included in a composition of the invention depends on various factors including, for example, the specific agent; function which it should carry out; required period of time for release of the agent; quantity to be administered. Generally, dosage of a therapeutically active agents, i.e., amount of therapeutically active agents in the system, is selected from the range of about 0.001% (w/w) to about 10% (w/w); about 1% (w/w) to about 5% (w/w); or about 0.1% (w/w) to about 1% (w/w).

The present invention also provides a system to encapsulate a device, or to coat a surface of a device. In particular, the hydrogel and the high density primary amine polymer and coupling agent are applied to the exterior surface of the hydrogel, and then the hydrogel is applied to the surface of the device. The coupling agent and the high density primary amine polymer adhere the hydrogel to the surface of the device. Depending upon to desired outcome, the device can be completely encapsulated by the hydrogel or partially encapsulated, leaving some surface of the device exposed. Specifically, a "partially encapsulated" device refers to coating the device either on one surface of the device (e.g., the back, front or sides of the device) or on one portion of the device (e.g., the bottom half or the top half). In a particular embodiment, the high density primary amine polymer and coupling agent may be applied to multiple sites of the hydrogel so that the hydrogel can adhere to both the device and also another surface (e.g., a tissue or organ). Exemplary medical devices include, but are not limited to a defibrillator, a pacemaker, a stent, a catheter, a tissue implant, a screw, a pin, a plate, a rod, an artificial joint, a elastomer-based (e.g., PDMS, PTU) device, a hydrogel-based device (e.g., scaffolds for drug or cell delivery or sensors), and sensors for measuring, for example, temperature, pH, and local tissue strains.

A surface can have functional groups (e.g., amine or carboxylic acid groups) or can be chemically inert. The biocompatible adhesive system of the invention can form electrostatic interactions, covalent bonds, and physical interpenetration with adherent surfaces. For substrates that bear functional groups like amines and carboxylic acids, adhesion can be formed via electrostatic interactions and covalent bonds between the TA and the substrate. For substrates that are hydrophilic and permeable to macromolecules, the high density primary amine polymers can interpenetrate into the substrate forming physical entanglements, and also form covalent bonds with the TA matrix.

The interfacial adhesion between the hydrogel and the surface (e.g., tissue or device) impacts the mechanical strength and reliability of the hydrogel, which corresponds to the performance of the hydrogel as an adhesive. The nature of this interaction can be measured as the interfacial fracture toughness. Methods to measure the interfacial fracture toughness are known to those of skill in the art. An exemplary method of measuring the interfacial fracture toughness is provided in Example 4. The systems of the present invention characterized by an interfacial toughness of from about 100 $J/m^2$ to about 5000 $J/m^2$, e.g., from about 100 $J/m^2$ to about 4500 $J/m^2$, from about 100 $J/m^2$ to about 4000 $J/m^2$, from about 100 $J/m^2$ to about 3500 $J/m^2$, from about 100 $J/m^2$ to about 3000 $J/m^2$, from about 100 $J/m^2$ to about 2500 $J/m^2$, from about 100 $J/m^2$ to about 2000 $J/m^2$, from about 100 $J/m^2$ to about 1500 $J/m^2$, from about 100 $J/m^2$ to about 1000 $J/m^2$, from about 100 $J/m^2$ to about 500 $J/m^2$, from about 500 $J/m^2$ to about 5000 $J/m^2$, from about 1000 $J/m^2$ to about 5000 $J/m^2$, from about 1500 $J/m^2$ to about 5000 $J/m^2$, from about 2000 $J/m^2$ to about 5000 $J/m^2$, from about 2500 $J/m^2$ to about 5000 $J/m^2$, from about 3000 $J/m^2$ to about 5000 $J/m^2$, from about 3500 $J/m^2$ to about 5000 $J/m^2$, from about 4000 $J/m^2$ to about 5000 $J/m^2$, from about 4500 $J/m^2$ to about 5000 $J/m^2$, from about 200 $J/m^2$ to about 3000 $J/m^2$, from about 1000 $J/m^2$ to about 3000 $J/m^2$, from about 2000 $J/m^2$ to about 3000 $J/m^2$, from about 200 $J/m^2$ to about 1000 $J/m^2$, from about 500 $J/m^2$ to about 1500 $J/m^2$, from about 1500 $J/m^2$ to about 3000 $J/m^2$, from about 2500 $J/m^2$ to about 3000 $J/m^2$, or from about 200 $J/m^2$ to about 1500 $J/m^2$.

In some embodiments, the biocompatible adhesive is transparent, allowing for ease of monitoring the surface below or the device encapsulated within. A photograph of the system of the invention is shown in FIGS. 12 and 13.

In some embodiments, the biocompatible adhesive is suitable for application to a surface that is wet, dynamic, or a combination of wet and dynamic.

A particular embodiment of the invention is a biocompatible adhesive system including a) a hydrogel comprising a first polymer network and a second polymer network, wherein the first polymer network comprises covalent crosslinks and the second polymer network comprises ionic crosslinks, wherein the first network comprises a polymer selected from the group consisting of polyacrylamide, poly (vinyl alcohol) (PVA), polyethylene glycol (PEG), and polyphosphazene; and the second network comprises an alginate polymer; b) a high density primary amine polymer selected from the group consisting of chitosan, gelatin, collagen, polyallylamine, polylysine, and polyethylamine; and c) a coupling agent comprising 1-ethyl-3-(3-dimethylaminopropyl)carbodiimide (EDC, EDAC or EDCI) and optionally N-hydroxysuccinimide (NHS).

In some embodiments, the biocompatible adhesive system is a layered adhesive. As used herein "a layered adhesive" means that the high density primary amine polymer and coupling agent are applied to one or more sides of the hydrogel. For example, the biocompatible adhesive system comprises a) a hydrogel comprising a first polymer network and a second polymer network, wherein the first polymer network comprises covalent crosslinks and the second polymer network comprises ionic crosslinks; b) a high density primary amine polymer; and c) a coupling agent, wherein the high density primary amine polymer and coupling agent are applied all sides of the hydrogel. A biocompatible adhesive system in which the high density amine polymer and coupling agent are applied to all sides of the hydrogel results in a hydrogel that is adhesive on all sides of the hydrogel. Alternatively, the biocompatible adhesive system comprises a) a hydrogel comprising a first polymer network and a second polymer network, wherein the first polymer network comprises covalent crosslinks and the second polymer network comprises ionic crosslinks; b) a high density primary amine polymer; and c) a coupling agent, wherein the high density primary amine polymer and coupling agent are applied to less than all of the sides of the hydrogel. A biocompatible adhesive system in which the high density amine polymer and coupling agent are applied to less than all sides of the hydrogel results in a hydrogel that is adhesive only on the sides of the hydrogel to which the high density amine polymer and coupling agent were applied. In particular, the biocompatible adhesive system comprises a) a hydrogel comprising a first polymer network and a second polymer network, wherein the first polymer network comprises covalent crosslinks and the second polymer network comprises ionic crosslinks; b) a high density primary amine polymer; and c) a coupling agent, wherein the high density primary amine polymer and coupling agent are applied to one side of the hydrogel. A biocompatible adhesive system in which the high density amine polymer and coupling agent were applied to only one side of the hydrogel is referred to as a "bilayered adhesive." A biocompatible adhesive system in which the high density amine polymer and coupling agent are applied to less that all of the sides of the hydrogel can be used when adhesion to side is required. In particular, the adhesive side (i.e., the side to which the high density amine polymer and coupling agent have been applied) may be placed on the surface (e.g., a tissue) to adhere the hydrogel to the surface. As the high density amine polymer and coupling agent was not applied to the rest of the hydrogel, the sides of the hydrogel not adhered to the surface are not adhesive, thereby avoiding any undesired adhesion.

The biocompatible adhesive could be engineered to be biodegradable (see Freier, T., Koh, H. S., Kazazian, K. & Shoichet, M. S. Controlling cell adhesion and degradation of chitosan films by N-acetylation. Biomaterials 26, 5872-5878 (2005); and Gong, J. P., Katsuyama, Y., Kurokawa, T. & Osada, Y. Double-network hydrogels with extremely high mechanical strength. Advanced Materials 15, 1155-+, doi: Doi 10.1002/Adma. 200304907 (2003), the teachings of which are incorporated herein by reference), and may be used to encapsulate drugs for controlled drug release; a further advantage of this system in certain applications is the transparency allows for easy visual monitoring.

III. Methods Of the Invention

The present invention also provides a method of adhering a hydrogel to a surface, the method including the steps of a) applying a solution comprising a high density primary amine polymer and a coupling agent to the hydrogel; and b) placing the hydrogel on the surface; wherein the hydrogel comprises a first polymer network and a second polymer network, wherein the first polymer network comprises covalent crosslinks and the second polymer network comprises ionic crosslinks. In certain embodiments, the surface is a tissue. The system can be applied to any tissue, including, but not limited to, heart tissue, skin tissue, blood vessel tissue, bowel tissue, liver tissue, kidney tissue, pancreatic tissue, lung tissue, trachea tissue, eye tissue, cartilage tissue, tendon tissue. Alternatively, the surface is a medical device. The system can be applied to any tissue, including, but not limited to, the group consisting of a defibrillator, a pacemaker, a stent, a catheter, a tissue implant, a screw, a pin, a plate, a rod, an artificial joint, a elastomer-based (e.g., PDMS, PTU) device, a hydrogel-based device (e.g., scaffolds for drug or cell delivery or sensors), and sensors for measuring, for example, temperature, pH, and local tissue strains.

The present invention also includes methods to encapsulate a medical device, or to coat a surface of a device. In particular, the hydrogel and the high density primary amine polymer and coupling agent are applied to the exterior surface of the hydrogel, and then the hydrogel is applied to the surface of the device. The coupling agent and the high density primary amine polymer adhere the hydrogel to the surface of the device. Depending upon to desired outcome, the device can be completely encapsulated by the hydrogel or partially encapsulated, leaving some surface of the device exposed. Specifically, a "partially encapsulated" device refers to coating the device either on one surface of the device (e.g., the back, front or sides of the device) or on one portion of the device (e.g., the bottom half or the top half). In a particular embodiment, the high density primary amine polymer and coupling agent may be applied to multiple sites of the hydrogel so that the hydrogel can adhere to both the device and also another surface (e.g., a tissue).

The present invention also method to close a wound or injury and promote wound healing. In particular, the hydrogel and the high density primary amine polymer and coupling agent are applied to the exterior surface of the hydrogel, and then the hydrogel is applied to the location of the wound or injury. In a particular embodiment, the hydrogel is applied to the heart in order to repair a heart defect.

The present invention also includes methods of delivering a therapeutically active agent to a subject, the method including a) applying a solution comprising a high density primary amine polymer and a coupling agent to a hydrogel; and b) placing the hydrogel on the surface; wherein the hydrogel comprises a first polymer network and a second polymer network, wherein the first polymer network comprises covalent crosslinks and the second polymer network comprises ionic crosslinks, and wherein at least one therapeutically active agent is encapsulated in, or attached to the surface of, the hydrogel and/or high density primary amine polymer, thereby delivering a therapeutically active agent to the subject.

The methods of the present invention include contacting the surface with a biocompatible adhesive. The surface can be contacted with the composition by any known routes in the art. As used herein, the term "delivery" refers to the placement of a composition into a subject by a method or route which results in at least partial localization of the composition at a desired site such that a desired effect is produced.

Exemplary modes of delivery include, but are not limited to, injection, insertion, implantation, or delivery within a scaffold that encapsulates the composition of the invention at the target surface, e.g., a tissue or organ. When the compositions of the invention are dissolved in a solution, they can be injected into the surface by a syringe.

The methods of the present invention are suitable for medical purposes, e.g., wound closure, delivery of a therapeutic agent, or attachment of a medical device, in a subject, wherein the subject is a mammal. In some embodiments, a mammal is a primate, e.g., a human or an animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, a subject is selected from the group consisting of a human, a dog, a pig, a cow, a rabbit, a horse, a cat, a mouse and a rat. In preferred embodiments, the subject is a human.

Exemplary modes of delivery include, but are not limited to, injection, insertion, implantation, or delivery within a scaffold that encapsulates the composition of the invention at the target tissue. In some embodiments, the composition is delivered to a natural or artificial cavity or chamber of a tooth of a subject by injection. When the compositions of the invention are dissolved in a solution, they can be injected into the tissue by a syringe.

In another aspect, the present invention provides a method of adhering a hydrogel to a surface (e.g., tissue or device), the method including the steps of a) applying a solution comprising a high density primary amine polymer and a coupling agent to the hydrogel; and b) placing the hydrogel on the surface; wherein the hydrogel comprises a first polymer network and a second polymer network, wherein the first polymer network comprises covalent crosslinks and the second polymer network comprises ionic crosslinks.

In particular, the coupling agent in solid form is added to an aqueous solution of the high density primary amine polymer and mixed for a specified period of time, e.g., 10 seconds, 30 seconds, 60 seconds, 2 minutes, 5 minutes, or 10 minutes. This solution is applied to the hydrogel. The treated surface of the hydrogel is then placed upon the surface, causing the hydrogel to adhere due to the formation of covalent bonds between the hydrogel, the high density amine polymer and the surface.

IV. Kits

The present invention also provides kits. Such kits can include a biocompatible adhesive described herein and, in certain embodiments, instructions for administration. Such kits can facilitate performance of the methods described herein. When supplied as a kit, the different components of the biocompatible adhesive system can be packaged in separate containers and admixed immediately before use. Components include, but are not limited to, a preformed hydrogel, a solution containing the high density primary amine component, and a coupling agent in solid form. In a particular embodiment, the present invention is directed to a three component system including a preformed alginate-based hydrogel; a dry powder mixture of EDC/NHS; and a aqueous solution of the high density primary amine polymer. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

In certain embodiments, kits can be supplied with instructional materials which describe performance of the methods of the invention. Detailed instructions may not be physically associated with the kit; instead, a user may be directed to an Internet web site specified by the manufacturer or distributor of the kit.

The present invention is further illustrated by the following examples, which are not intended to be limiting in any way. The entire contents of all references, patents and published patent applications cited throughout this application, as well as the Figures, are hereby incorporated herein by reference.

EXAMPLES

Example 1. Synthesis of Biocompatible Adhesives

Materials. High molecular weight sodium alginate ($M_w$=265 kDa) with high guluronate content (Protanol LF 20/40; FMC Technologies) was used for all adhesion and in vitro experiments. Low molecular weight of sodium alginate was prepared by irradiating the high molecular weight sodium alginate (Protanol LF 20/40; FMC Technologies) under γ-rays at a dose of 5 Mrad following the protocol as described in Kong, H. J., Kaigler, D., Kim, K. & Mooney, D. J. Controlling rigidity and degradation of alginate hydrogels via molecular weight distribution. *Biomacromolecules* 5, 1720-1727 (2004), the entire teachings of which are herein incorporated by reference. Ultrapure sodium alginate with low endotoxin levels (MVG alginate, ProNova Biomedical AS) was used for in vivo adhesion measurements. Chitosans of low, medium and high molecular weights were purchased from Sigma, except the ultrapure chitosan for in vivo experiments which was purchased from ProNova Biomedical AS. The high density amine polymers polyallylamine, gelatin, and polyethyleneimine were purchased from Sigma, and type I collagen was purchased from Advanced BioMatrix. The coupling agents 1-ethyl-3-(3-dimethylaminopropyl) carbodiimide hydrochloride (EDC) and N-hydroxysulfosuccinimide (sulfo-NHS) were purchased from ThermoFisher Scientific. Medical grade cyanoacrylate (Loctite 4541 Prism) was purchased from Henkel Corporation. Monomers including acrylamide (AAM), N,N'-methylenebis(acrylamide) (MBAA), polyhydroxyethylmethacrylate (HEMA), free-radical initiator ammonium persulfate (APS), and polymerization accelerator tetramethyl-ethylenediamine (TEMED) were purchased from Sigma. Polyethylene glycol diacrylate (PEGDA-20 kDa) was synthesized according to the protocol described in Nemir, S., Hayenga, H. N. & West, J. L. PEGDA hydrogels with patterned elasticity: Novel tools for the study of cell response to substrate rigidity. *Biotechnology and Bioengineering* 105, 636-644 (2010), the entire teachings of which are incorporated herein by reference. Fluorescein isothiocyanate-labeled chitosan (FITC-chitosan) was synthesized according to the protocol described in Qaqish, R. B. & Amiji, M. M. Synthesis of a fluorescent chitosan derivative and its application for the study of chitosan-mucin interactions. *Carbohydrate Polymers* 38, 99-107 (1999), the entire teachings of which are incorporated herein by reference. Fluorescent microspheres of 500 nm diameter with carboxylic acid functional groups were purchased from ThermoFisher Scientific. Porcine skin and liver was purchased from a local grocery store.

Synthesis. To prepare the biocompatible adhesive, a bulk hydrogel was preformed, and then its surface was treated with an aqueous solution of the high density primary amine polymer and coupling agents for the carbodiimide coupling reaction. The alginate-polyacrylamide hydrogels were prepared according to the protocol described in Li, J., Illeperuma, W. R. K., Suo, Z. & Vlassak, J. J. Hybrid Hydrogels with Extremely High Stiffness and Toughness. *ACS Macro Lett.* 3, 520-523 (2014), the teachings of which are incorporated herein by reference. The ratio of the high and low molecular weight alginates was fixed at 50:50. The high density primary amine polymers polyallylamine, chitosan, gelatin, and polyethyleneimine were dissolved into MES buffer at 2.0 wt % and the pH was adjusted to 6. The collagen was used as a stock solution (1.0 wt % and pH=2.0). The coupling agents used were 1-ethyl-3-(3-dimethylaminopropyl) carbodiimide (EDC), sulfated or non-sulfated N-hydroxysuccimide (NHS), and the final concentrations of EDC and Sulfated NHS in the solution of bridging polymer were both 12 mg/mL. The solution of the bridging polymer and coupling agents (~250 μL) was applied to the surface of the bulk matrix (15×70 mm²) for 1 minute prior to applying the biocompatible adhesive to the surface of interest. A gentle compression was applied, typically for 30 mins unless stated otherwise, before mechanical testing.

Example 2. Biocompatible Adhesives

Figure 1:
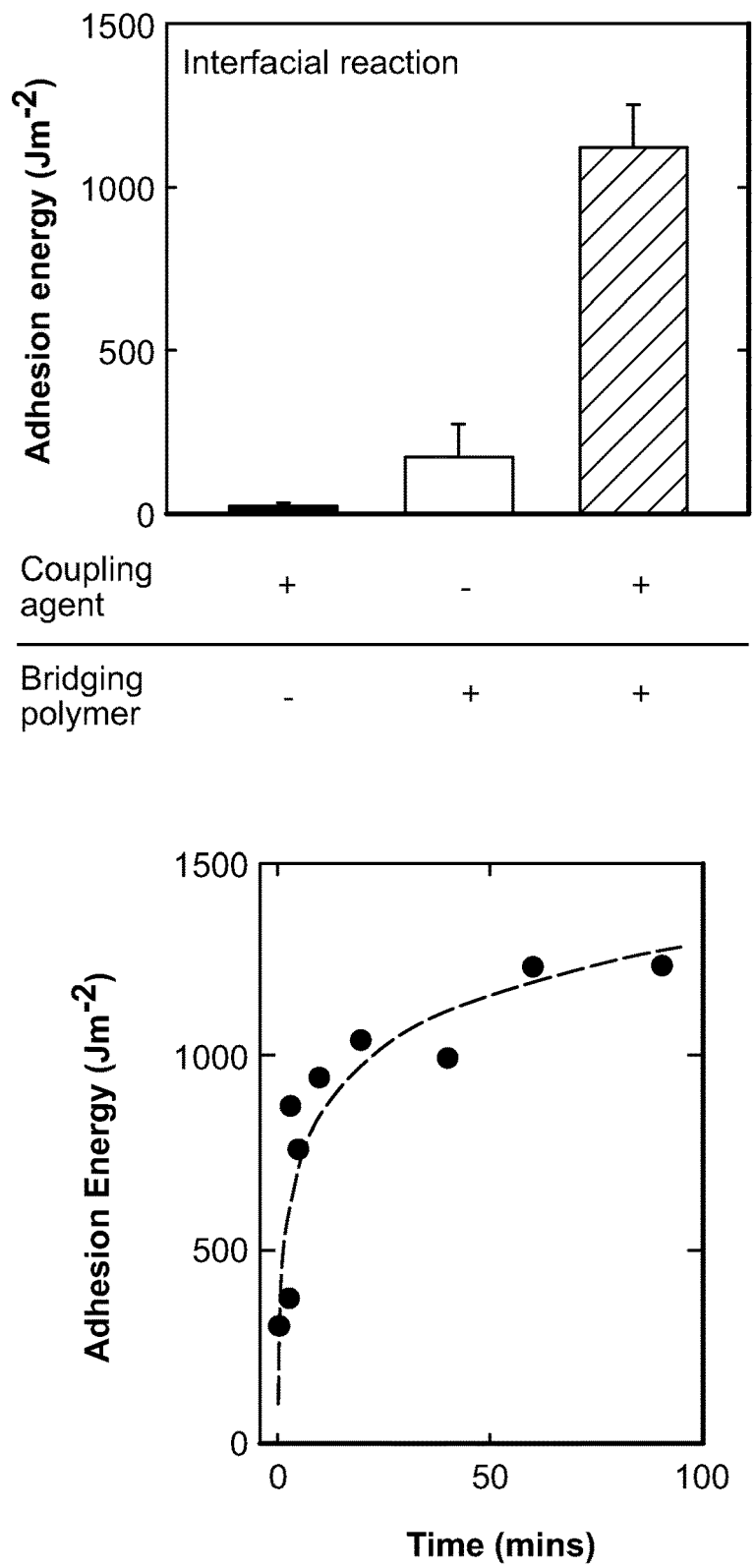

The superior adhesiveness of the biocompatible adhesive system of the invention relative to hydrogels is shown in FIG. 1. Chitosan is a representative high density primary amine polymer. The adhesive properties of chitosan are compared with and without the inclusion of a representative coupling agent used in the present invention. The treatment of chitosan with EDC/NHS results in stronger adhesion as compared to chitosan alone or EDC/NHS alone (FIG. 1, top). Both EDC and sulfo-NHS were dissolved in 2 wt % chitosan aqueous solution to 12 mg/mL, and then 0.2 mL of the mixture was applied to a tissue surface (like porcine skin) of 25 mm×75 mm.

As shown in FIG. 1, use of the coupling reagents EDC/Sulfo-NHS alone led to very low adhesion energy; without the high density primary amine polymer (i.e., chitosan), the hydrogel matrix is likely to be repelled electrostatically by the negatively charged tissue surfaces. C. K. Roy et al., *Adv. Mater.* 27, 7344-7348 (2015). The bridging polymer without the coupling reagents also led to low adhesion energy. The purely electrostatic attraction in this situation is not as strong as covalent bonds bridging the two surfaces. In contrast, the tough adhesive consisting of both the bridging polymer and the coupling reagents led to an extremely high adhesion energy. These results emphasized the importance of both electrostatic attraction and covalent bonds for strong adhesion (FIG. 23). This finding also indicated that it is feasible to design the adhesives with adhesive and non-adhesive regions by selectively patterning the bridging polymer onto the hydrogel surface. This result also shows the surface of the hydrogel can be selectively modified with adhesive and non-adhesive regions by selectively patterning the high density primary amine polymer onto the hydrogel surface. Selective patterning of adhesive sections on the hydrogel surface can be used to prevent unwanted adhesions between tissues in certain situations. The adhesion as measured by the interfacial toughness forms within 5 minute, and become stronger with time (FIG. 1, bottom). The biocompatible adhesive exhibits a rapid increase in adhesion energy to porcine skin over time, with a value of 300 $Jm^{-2}$ within one minute; it further increased to 1000 $Jm^{-2}$ within 30 minutes. This rapid, but not immediate adhesion is likely to aid clinical translation and adoption of these tissue adhesives, as it allows the material to be applied in a facile manner. In contrast, cyanoacrylate solidifies upon contact with tissues, which makes handling and repositioning difficult.

Example 3. Interfacial Toughness of High Density Primary Amine Polymers

Figure 2:
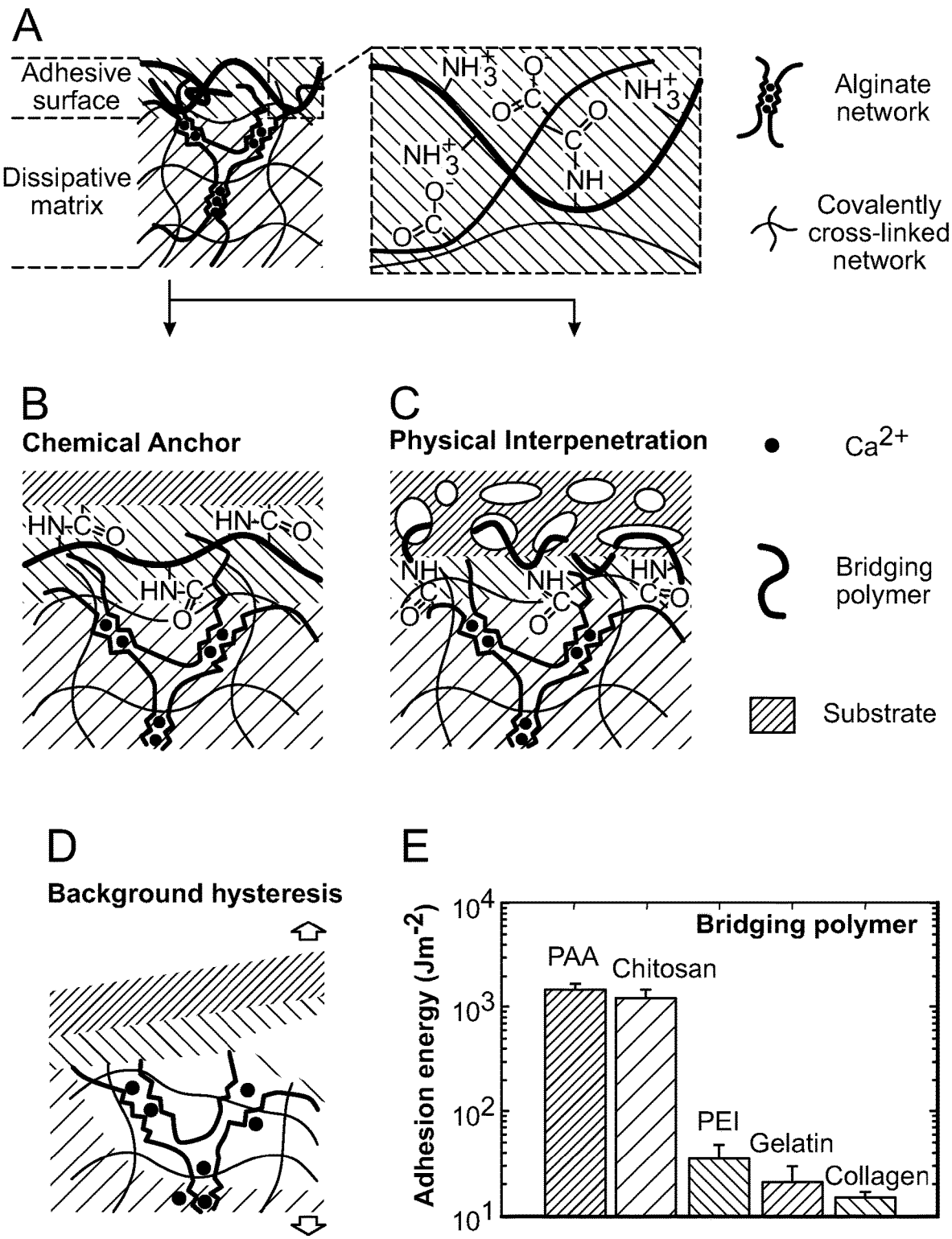

The interfacial toughness of five representative high density amine polymers are compared in FIG. 2€. Porcine skin was used as a model tissue. Five polymers that carry high density amine groups were dissolved in water to 2 wt %. Each solution was mixed with EDC and sulfo-NHS, which were at the final concentration of 12 mg/mL respectively. The mixture was used to activate alginate-polyacrylamide hydrogels for 15 mins before performing standard peeling tests to measure the interfacial toughness.

Example 4. Adhesive Strength of Biocompatible Adhesives

Figure 3:
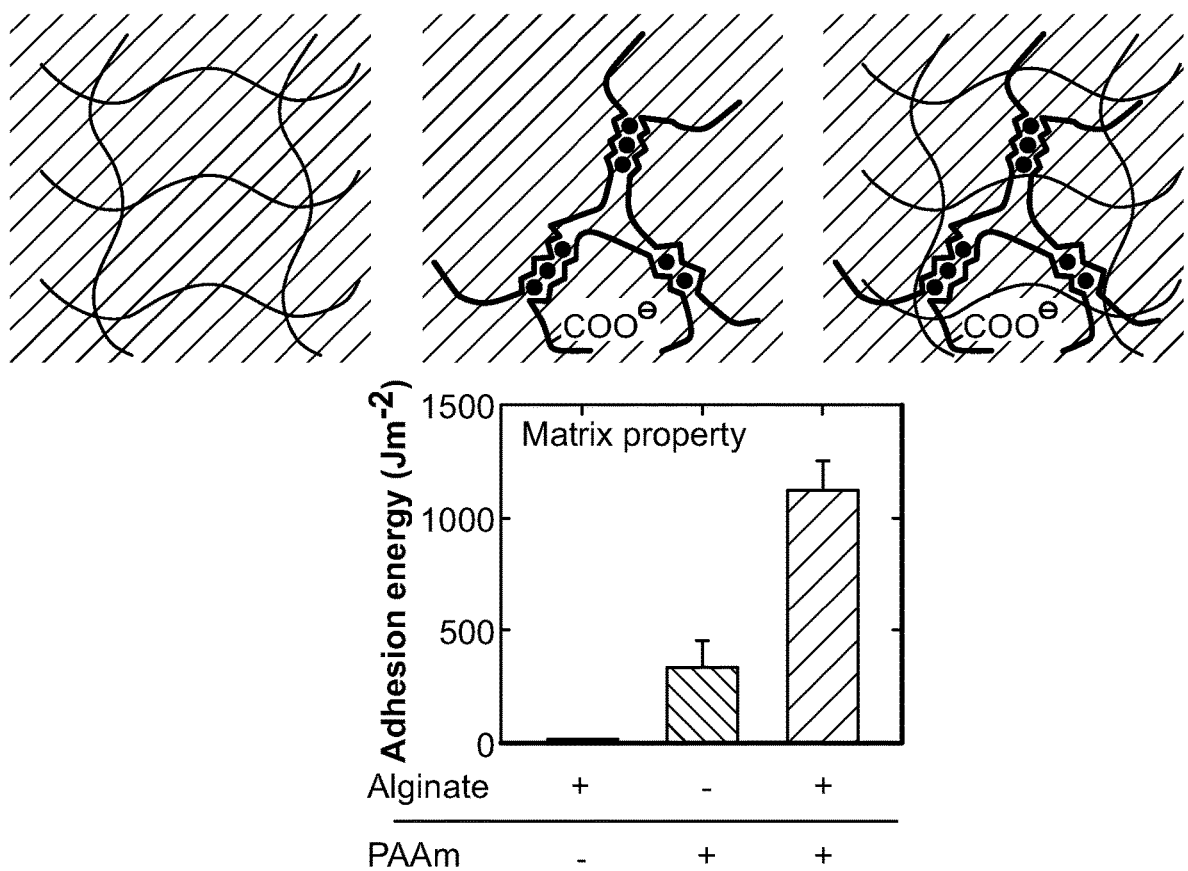

Hydrogels based upon an interpenetrating network (IPN) of a first polymer network and a second polymer network provides the superior adhesion compared to either the first polymer network or the second polymer network alone. A schematic of the three hydrogels tested is shown in FIG. 3. A first polymer network including only covalent crosslinks is depicted in FIG. 3, top left. A second polymer network including only ionic crosslinks is depicted in FIG. 3, top center. An IPN network including both the first and second polymer networks is depicted in FIG. 3, top right.

Adhesives formed with either single-network polyacrylamide (PAAM) hydrogels and alginate hydrogels, or hydrogels comprised of both polymer networks were compared. The PAAM hydrogel was prepared by free radical copolymerization of acrylamide and N,N'-methylenebisacrylamide. The alginate hydrogel was prepared by mixing sodium alginate aqueous solutions and calcium sulfate slurries. The combination of the two reactions led to the IPN hydrogel. In the measurements, the surface of hydrogels was treated with the activation agents, in which chitosan was at 2 wt %, EDC and sulfo-NHS were at 12 mg/mL; then the activated hydrogels were attached to porcine skin, followed with standard peeling tests to measure the force-extension curves. The value of interfacial toughness was two-fold of the ratio of force to sample width at the steady state.

As shown in FIG. 3, bottom, adhesives fabricated from single-network hydrogels exhibited low adhesion energy, as they lack effective energy dissipating mechanisms that can toughen the interface. The interfacial toughness of the IPN hydrogel based upon alginate and polyacrylamide (PAAM) was greater than hydrogels based upon only PAAM or alginate alone. These results support the hypothesis that combining electrostatic and covalent bonds, and background hysteresis of the bulk hydrogel contributes to high adhesion energy.

Example 5. Effect of Molecular Weight of Alginate

Figure 4:
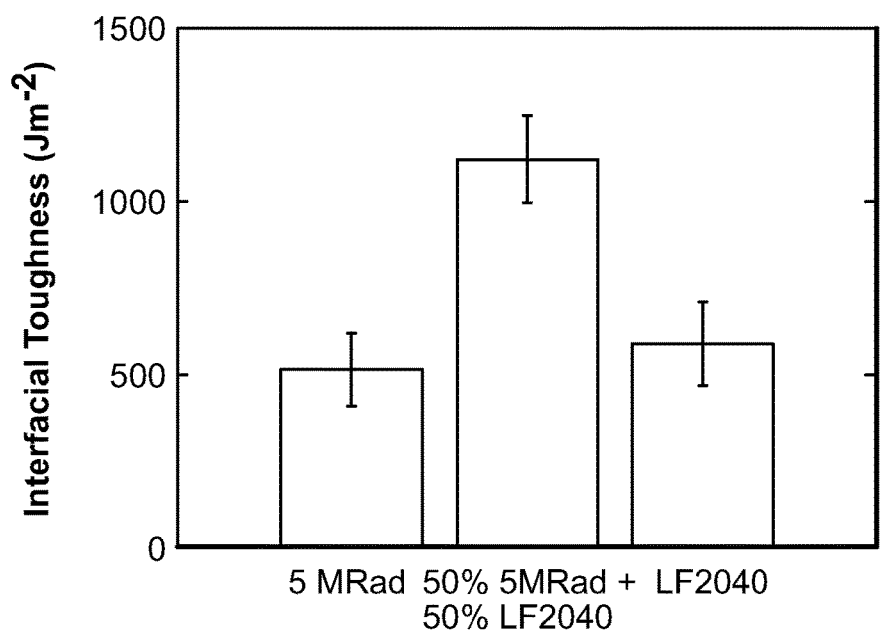

The molecular weight of the first and second network polymers can be tuned to modulate the interfacial toughness of the adhesive system. The alginate-polyacrylamide IPN hydrogel was chosen as a model tough hydrogel. The 3 hydrogels comprise the same compositions, except for the molecular weight of alginate that used to form the second network. The alginate was tuned by mixing high and low molecular weight chains, while the total concentration of alginate was fixed around 2 wt %. The alginate of high molecular weight (~200 kDa) was denoted as LF2040, while that of low molecular weight (~20 kDa) was denoted as 5MRad. In the measurements, the surface of hydrogels was treated again with the activation agents, in which chitosan was at 2 wt %, EDC and sulfo-NHS were at 12 mg/mL; then the activated hydrogels were attached to porcine skin, followed with standard peeling tests to determine the interfacial toughness. An optimal value exists for 50% low molecular weight alginate (~20 kDa) and 50% high molecular weight alginate (~200 kDa) (FIG. 4).

Example 6. Adhesive Peeling Test

Adhesion Energy Measurements. The adhesive property of the tough adhesive was quantified as adhesion energy, namely the amount of energy required to increase a unit area of interfacial crack. The adhesion energy was determined with either peeling adhesion tests, or bilayer adhesion tests when the substrate had low bulk toughness.

Peeling Adhesion Test. The adhesion energy was measured with 180 degree peeling tests. A ribbon of the tough adhesive (15×1.5×80 $mm^3$) was adhered to a substrate with one end open, forming a bilayer with an edge crack. The back of the tough adhesive was also bonded to a rigid polyethylene terephthalate film with Krazy Glue, in order to limit deformation to the crack tip, and thus all the work done by the machine would be equal to the energy dissipated at the crack tip. The free ends of the tough adhesive and the substrate were attached to plastic sheets, to which the machine grips were attached. An Instron machine was used to apply unidirectional tensile tests, while recording the force and the extension. The loading rate was kept constant at 100 mm/min. The adhesion energy was two-fold the plateau value of the ratio of the force and width. R. S. Rivlin, A. G. Thomas, *J. Polym. Sci.* 10, 291-318 (1953)

Bilayer Adhesion Test. When hydrogels of low bulk toughness were tested, a bilayer adhesion test was used to measure adhesion energy. The tested hydrogels include alginate-polyacrylamide, polyacrylamide and polyhydroxyethyl methacrylate hydrogels. The bilayer specimens were prepared by compressing a tough adhesive of 45 mm×20 mm×1.5 mm on a hydrogel of 45 mm×20 mm×1.5 mm. A rigid polyethylene terephthalate (PET) thin film with thickness 120 μm (Transparency Copy Film, PP2500, 3M) were glued to the testing hydrogel as a backing layer by Krazy glue. The specimen was stretched by an Instron machine with a constant loading rate of 0.5 mm/s, while the force-stretch curves were recorded. The adhesion energy can be calculated by $G=P(\lambda-1)-U_s(\lambda)$, where P and $\lambda$ are the critical force per unit width (the force in the current state divided by the width of the sample in the undeformed state) and critical stretch when debonding occurs (J. Tang, J. Li, J. J. Vlassak, Z. Suo, *Soft Matter* 12, 1093-1099 (2016)). $U_S$ is the strain energy stored in the substrate divided by the area of the substrate in the undeformed state when debonding occurs, which is the area under the recorded force-stretch curve with stretch from 1 to $\lambda$.

Figure 5:
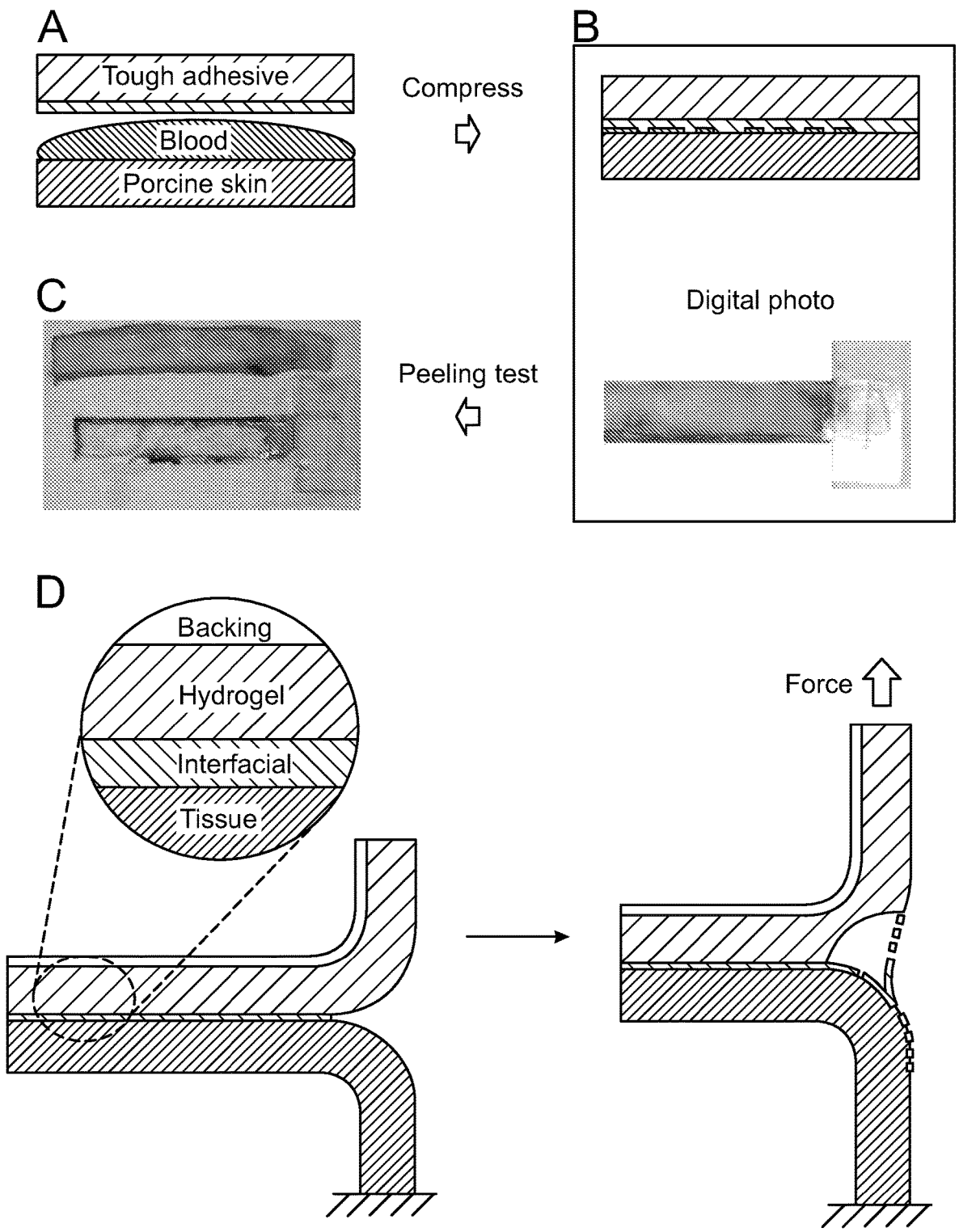
Figure 7:
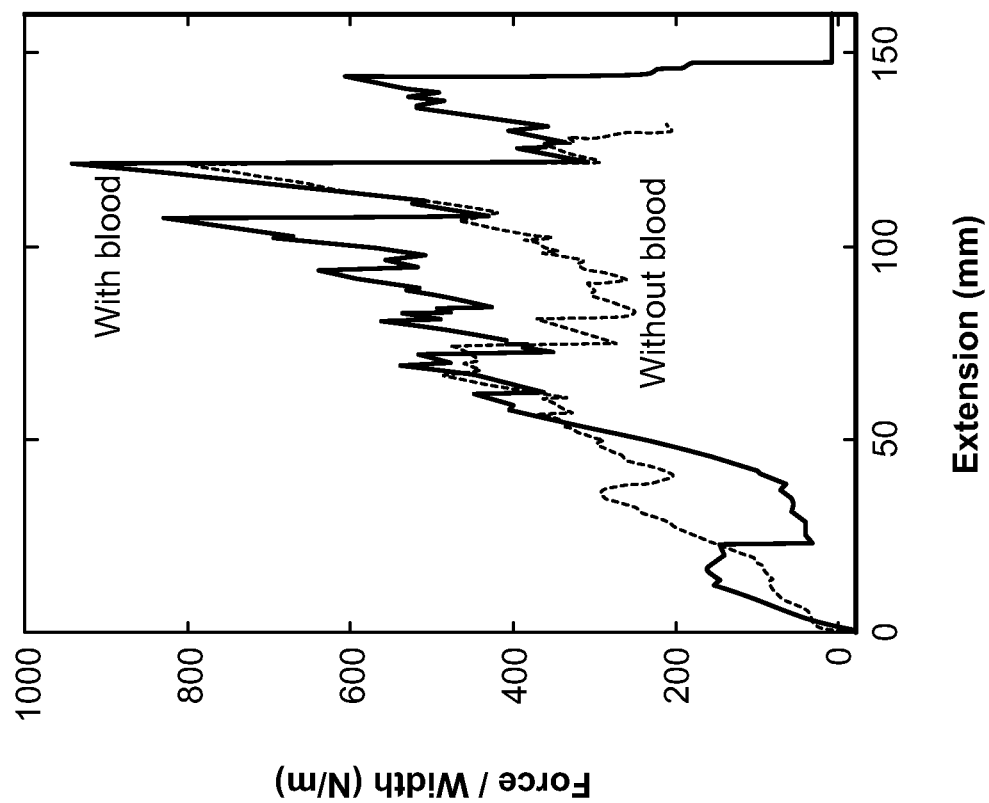
FIG. 7 is a plot of the interfacial toughness of a biocompatible adhesive of the present invention as measured in the presence or absence of blood.
Figure 6:
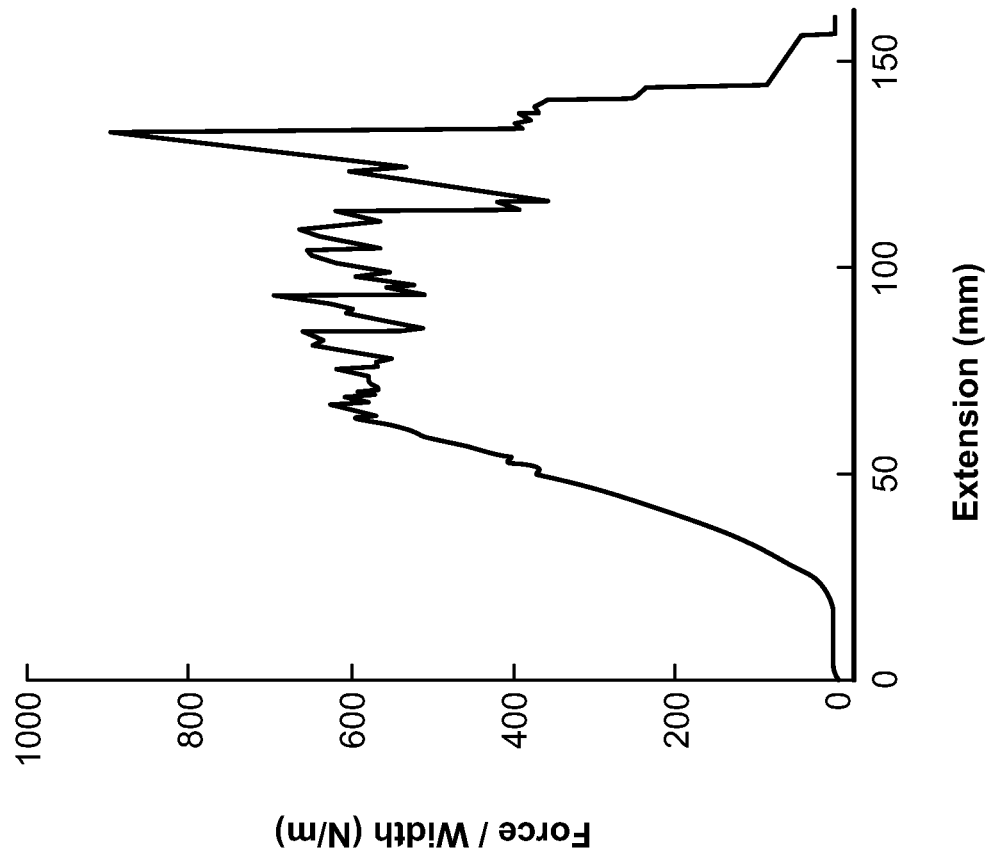
FIG. 6 is a plot of the interfacial toughness of a biocompatible adhesive of the present invention.

To assess the adhesion property of the system of the present invention, peeling tests on bilayers of the system and porcine skin were conducted. Interfacial toughness was adopted to quantify the adhesion property, which was measured with standard peeling tests (as described above). The interfacial toughness is defined as the energy required to extend a unit area of crack at the interface, reflecting how strong an interface resists debond. The peeling test has been widely used to assess the adhesion performance of commercial adhesives and glues. A schematic representation of the test is presented in FIG. 5D. In particular, a specimen was typically a piece of adhesive hydrogel sandwiched with porcine skin and plastic film. The adhesive side of the hydrogel was attached to the tissue, in particular, the system, including the hydrogel, high density amine polymer and coupling agent were applied to porcine skin. The plastic film was used as a rigid backing to limit the dissipated energy concentration at the interface. The force required to peel the system off of the porcine skin and the extension of the hydrogel were then measured with an Intron machine. From the measured force-extension curves, two-fold of the ratio of force to sample width at the steady state gives the value of interfacial toughness.

Example 7. Effect of Blood Exposure

The formation of tissue adhesion is often complicated under in vivo conditions due to exposure to liquids (e.g., blood), and dynamic movements of tissues. See N. Lang et al., *Sc. Transl. Med.* 6, 218ra216 1-10 (2014). To assess the adhesive performance with the exposure to blood, the surface of porcine skin was initially covered with or without blood (FIG. 5A-5C), followed with the implement of the biocompatible adhesive of the present invention, and the commercial adhesive (cyanoacrylate). The surface of the IPN hydrogel (25 mm×75 mm) was cast 0.2 mL volume of either the activate agent (chitosan and EDC/sulfo-NHS), or the cyanoacrylate. In these measurements, the hydrogel was an alginate-polyacrylamide hydrogel, the high density primary amine polymer was chitosan, and the coupling agent is EDC and sulfo-NHS.

Figure 9:
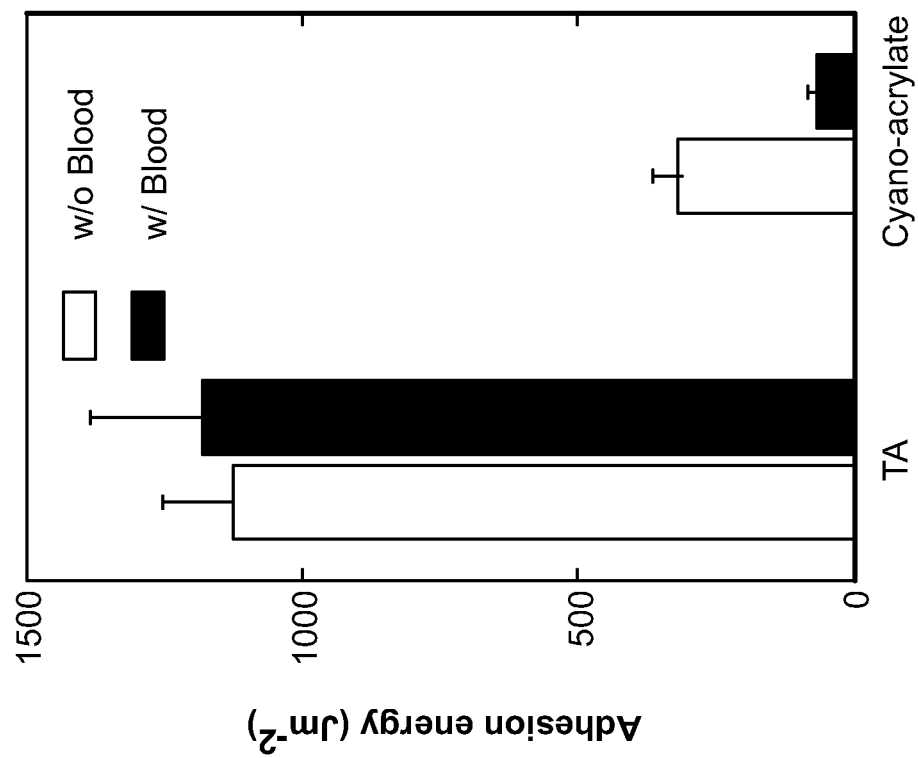
FIG. 9 is a plot comparing the interfacial toughness of the commercial adhesive, cyanoacrylate, to the biocompatible adhesive of the present invention. Error bars show standard deviation.
Figure 8:
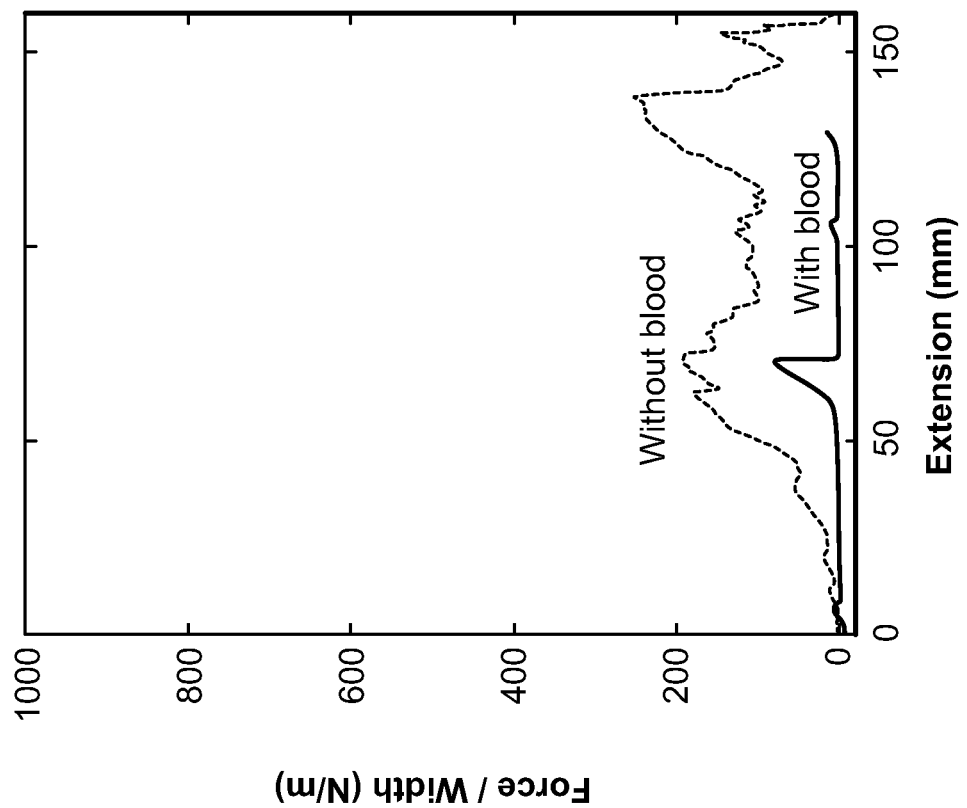
FIG. 8 is a plot of the interfacial toughness of the commercial adhesive, cyanoacrylate, as measured in the presence or absence of blood.

After adhesion, and upon mechanical stretching, the interface between the skin and biocompatible adhesive exhibited fibrillar structures, indicating large deformation was still possible without rupture of the adhesion. A plot of the interfacial toughness of a biocompatible adhesive of the present invention, and the commercial adhesive (cyanoacrylate) as measured in the presence or absence of blood are shown in FIGS. 6-9. As demonstrated in FIG. 9, the adhesive-skin interface exhibited an extremely large adhesion energy of ~1200 $Jm^{-2}$, and insensitive to the blood, indicating that the biocompatible adhesive is capable of robust adhesion even with blood exposure. In contrast, the adhesion provided by the widely used cyanoacrylate led to a much lower adhesion energy of ~300 $Jm^{-2}$ and deteriorated significantly upon exposure to blood. The adhesion energy decreased from 300 $Jm^{-2}$ to 50 $Jm^{-2}$ (FIG. 9).

In sum, the biocompatible adhesive of the present invention adheres strongly to the surfaces of tissues such as skin and heart, sustaining significant mechanical loads and strains even with the exposure of blood.

Example 8. Biocompatiblity

To assess the biocompatiblity of the adhesive hydrogel in the present invention, in vitro cell viability tests were conducted with normal human dermal fibroblasts (HDF) from adult and neonatal tissue (Lonza). The IPN hydrogels with and without the activation agent (chitosan and EDC/sulfo-NHS) were soaked in cell culture media DMEM, along with cyanoacrylate for comparison. After 24 hours, the media was collected, and used as conditioned media in cell culture. The conditioned media of 100 μL was added per well, in which the HDF was seeded at 12 k per well. After 24-hour culture, live/dead staining was performed with the Live/Dead Viability/Cytotoxicity Kit (Life Technologies) per the manufacturer's instructions (FIG. 10). Both the original IPN and the adhesive IPN hydrogels led to very high cell viability (>95%, live cells in green elongated form, FIG. 10, left and center) and good proliferation. However, the cyanoacrylate caused significant reduction of cell viability and proliferation (FIG. 10, right, dead cells in red dot form).

Example 9. Repair of Heart Defects

The present invention can be used as a sealant to repair heart defects. The biocompatible system of the present invention is very compliant and conforms to the curved surfaces of organs such as the heart. The stretchability of hydrogel used in the present invention and the strong adhesion guarantee a perfect sealing even under large static and dynamic deformation A schematic of the creation and closure of the heart defect is depicted in FIG. 11. Liquid flows through the hole created in the heart (FIG. 12, top). Application of biocompatible system blocks the flow of liquid through the hole, even when pressure is applied to the heart indicating sealing of the hole under large strains (~100%) (FIG. 12, center). The hole remains sealed even under high-frequency dynamic deformation (FIG. 12, bottom). Moreover, the biocompatible system of the present invention is transparent, allowing for continuous monitoring of the surface without requiring removal of the hydrogel (FIG. 12, top, center, and bottom).

A circular defect of 7 mm diameter was created on the ventricular wall of a porcine myocardium and this was then sealed by adhering a biocompatible adhesive of the present invention (PAAM/Alginate/Chitosan/EDC) to the myocardium as a patch (as shown in in FIG. 12, center and bottom). The biocompatible adhesive was compliant and conformed closely to the geometry of the myocardium. To determine the quality of the seal, PBS was flowed into the heart. While the heart was being inflated, the hydrogel expanded with the deformation of the heart, and no leakage was observed under strain up to 100% (FIG. 12, center). The biocompatible adhesive patch also accommodated high frequency movement of the heart, as demonstrated during multiple cycles of inflation-deflation (FIG. 12, bottom). The typical physiological strain of a working heart is around 10-30%, (see Aletras, A. H., Balaban, R. S. & Wen, H. High-resolution strain analysis of the human heart with fast-DENSE. *Journal of Magnetic Resonance* 140, 41-57 (1999), the teachings of which are incorporated herein by reference) and the biocompatible adhesive remained adherent well above this range.

To further evaluate the potential of the biocompatible adhesive as a tissue adhesive, its adhesion to a porcine heart was tested in vivo. Freshly drawn porcine blood was spread on the surface of the heart at the site of application, followed by application of the biocompatible adhesive. A peeling test was performed with the force recorded during pulling, and the results demonstrated a strong adhesion was formed on the dynamic curved heart surface with a peak strength of 83.5 kPa, which exceeds all current commercially available tissue adhesives (typically ~10 kPa). (for commercial adhesives, see Lang, N. et al. A blood-resistant surgical glue for minimally invasive repair of vessels and heart defects. *Science translational medicine* 6, 218ra216-218ra216 (2014), the teachings of which are incorporated herein by reference).

Methods. Female Yorkshire swine with a body weight of 60-75 kg were used. All animals received humane care in accordance with the 1996 Guide for the Care and Use of Laboratory Animals recommended by the US National Institute of Health. The experimental protocol was approved by the Boston Children's Hospital Institutional Animal Care and Use Committee. The pigs were anesthetized by intramuscular injection of tiletamine/zolazepam (7 mg/kg) and xylazine (4 mg/kg), intubated with a cuffed endotracheal tube and ventilated with a volume control ventilator (Hallowell EMC Model 2000, Hallowell EMC, Pittsfield, MA) at a rate of 10-20 breaths per minute. Anesthesia was maintained with isoflurane (1-2%). Fentanyl and Buprenorphine were used for analgesia. A maintenance IV infusion of 150-300 ml per/hour was administered. The chest cavity was accessed via midline sternotomy and the pericardium was opened to expose the heart surface. The biocompatible adhesives were applied to the beating heart surface and held in place to 3 minutes using an applicator. This application did not affect heart function. In some of the experiments, blood was added to the surface of the heart prior to applying the biocompatible adhesive in order to assess the effect of the presence of blood.

Thus, the combination of strong adhesion, large stretchability, transparency and biocompatibility makes the biocompatible system of the present invention superior or many biomedical applications such as wound closure, healing and repair of heart defects to the present biological adhesives.

Example 10. Medical Tape/Bandage

The biocompatible system of the present invention can be used as a medical tape to adhere to encapsulate actuator devices (FIG. 13, top) and attach them on the heart surface (FIG. 13, center and bottom), to close and heal a wound, or to replace sutures used in anastomosis with the biocompatible systems of the present invention.

Example 11. Injectable Biocompatible Adhesives

To make the adhesive hydrogel injectable, PEG and click chemistry was used to replace the polyacrylamide as the first cross-linked network in the IPN hydrogels. An injectable adhesive was prepared with PEG modified with norborne and PEG modified with tetrazine in the presence of alginate. The PEG-norborne has 4 arms with norborne groups at each end. The PEG-tetrazine is bifunctional with tetrazine at the ends. A PEG-alginate IPN was formed upon addition of $CaSO_4$ (FIG. 14). Alternatively, the biocompatible system can be prepared upon exposure of UV light. Bifunctional PEG with thiol ending groups was used instead of the PEG-tetrazine. A PEG-alginate IPN was prepared with PEG-norborne and PEG-thiol in the presence of alginate (FIGS. 15 and 16).

Example 12. Confocal Imaging of Adhesion Interface

A biocompatible adhesive system was prepared using FITC-chitosan as the high density primary amine polymer and PAAM-alginate IPN as the hydrogel, and adhered to porcine skin, porcine muscle or hydrogels. Adhesion was performed in the dark, and allowed to develop for one hour. The samples were cryo-protected in 20% sucrose/PBS at room temperature and embedded in OCT before being frozen on dry ice. Transverse cryosections (50 μm) were cut using a cryostat (Leica CM1950) and imaged by confocal fluorescence microscopy (Zeiss LSM710). The excitation wavelength of FITC was set to be 490 nm, and bright field images were also collected.

As the biocompatible adhesives can potentially provide adhesion to even chemically inert surfaces, the physical interpenetration of the high density primary amine polymer with the surface to which adhesion is desired was studied. Unlike tissues, certain hydrogels (e.g., polyacrylamide or polyhydroxyethyl methacrylate) lack the functional groups (e.g., amine or carboxylic acid) utilized here to form chemical bonds at the interface, but interestingly they still adhere well to TA (FIG. 24). The adherence of the biocompatible adhesive to a representative tissue, skin, and a chemically inert hydrogel, polyacrylamide was studied. Strong adhesion of the biocompatible adhesive to both was found and is shown in FIG. 17, top. While the high density primary amine polymer was found to interpenetrate into a variety of substrates, the distance of interpenetration in a given time was dependent on the substrate permeability; as hydrogels are more permeable than the skin, the depth of physical interpenetration in hydrogels at a given time was larger than found in skin (FIG. 18).

The biocompatible adhesive is applicable to a wide variety of biological tissues and hydrogels, and the toughness of the substrates to which it adheres sets an upper bound for the adhesion energy. Indeed, when alginate-polyacrylamide hydrogels were used as the substrate (see Sun, J. Y. et al. Highly stretchable and tough hydrogels. Nature 489, 133-136, doi:Doi 10.1038/Nature11409 (2012), and Li, J., Illeperuma, W. R., Suo, Z. & Vlassak, J. J. Hybrid Hydrogels with Extremely High Stiffness and Toughness. ACS Macro Letters 3, 520-523 (2014), the entire teachings of both are incorporated herein by reference), the adhesive achieved an extremely high adhesion energy on the order of 1000 Jm$^{-2}$. In this situation, the performance of the biocompatible adhesive was similar to the adhesion of cartilage to bone or muscle. Alternatively, the adhesion strength was similar to the bulk toughness of the substrate if the substrate toughness was not greater than that of the biocompatible adhesive itself (e.g., adhesion to PHEMA) (FIG. 17, bottom).

To compare the biocompatible adhesive of the present invention with other existing adhesives, cyanoacrylate provides high bulk toughness, but limited adhesion energy (see Stefanov, T., Ryan, B., Ivanković, A. & Murphy, N. Mechanical bulk properties and fracture toughness of composite-to-composite joints of an elastomer-toughened ethyl cyanoacrylate adhesive. International Journal of Adhesion and Adhesives 68, 142-155 (2016), the entire teachings of which incorporated herein by reference); nanoparticles and mussel-inspired adhesives based on polyethylene glycol hydrogels are relatively brittle, and provide low adhesion energy on tissues (FIG. 17, bottom) See Rose, S. et al. Nanoparticle solutions as adhesives for gels and biological tissues. Nature (2013); Barrett, D. G., Bushnell, G. G. & Messersmith, P. B. Mechanically robust, negative—swelling, mussel—inspired tissue adhesives. *Advanced healthcare materials* 2, 745-755 (2013); and Yuk, H., Zhang, T., Lin, S., Parada, G. A. & Zhao, X. Tough bonding of hydrogels to diverse non-porous surfaces. *Nature materials* 15, 190-196 (2016), the entire teaching of all are incorporated herein by reference. The biocompatible adhesive of the present invention demonstrates exceptional adhesive properties, and there exists a wide range of wet surfaces to which it can adhere.

Example 13. Adherence to Liver Tissue and Skin

To further test the potential of the biocompatible adhesive as a tissue adhesive, it was adhered to liver tissue and skin. A slice of liver was adhered to two biocompatible adhesive that were subsequently subjected to tensile testing. The biocompatible adhesive remained highly stretchable and sustained 14 times its initial length without debonding from the liver tissue (FIG. 19). In addition, the biocompatible adhesive adhered strongly to the intact epidermis of mice, and readily accommodated the dynamic movement of this tissue on the living animal.

Methods. All work was done with C57BL/6J mice (female, aged 6-8 weeks; Jackson Laboratories) and was carried out in accordance with the Institute for Animal Care and Use Committee, Harvard University, and National Institutes of Health and institutional guidelines. Mice were anesthetized, and shaved part of dorsum where two pieces of tough adhesives of 6 mm diameters were applied with a custom designed applicator for 2 minutes. Anesthesia was maintained with isoflurane (1-2%). The mice were returned to their cages after recovery from anesthesia. Videos were recorded to assess the adhesion under movement of mice.

Example 14. In Vivo Biocompatibility Test

The in vivo biocompatibility of the biocompatible adhesive was tested by adhering to living rat myocardium for 2 weeks. The biocompatible adhesive led to dramatically lower inflammation than the standard cyanoacrylate adhesive (FIG. 20). These findings suggest biocompatible adhesive may also enable immobilization of biomedical devices, such as actuators, onto tissues like the heart.

This study, involving Female Sprague Dawley rats (225-275 g) was carried out in accordance with the Institute for Animal Care and Use Committee, Harvard University. In brief, the epicardial surface was exposed and the heart was manipulated as previously described. (See Roche, E. T., Hastings, C. L., Lewin, S. A., Shvartsman, D. E., Brudno, Y., Vasilyev, N. V., O'Brien, F. J., Walsh, C. J., Duffy, G. P., Mooney, D. J. Comparison of biomaterial delivery vehicles for improving acute retention of stem cells in the infarcted heart. *Biomaterials* 35, 6850-8 (2014), the teachings of which are incorporated herein by reference) Biocompatible adhesives or cyanoacrylate plus alginate-polyacrylamide hydrogels were compressed against the epicardial surface using a custom made applicator to allow the adhesive to set. The incisions in the animals were closed with sutures, and animals were returned to their cages after recovery from anesthesia. Two weeks later, hearts were explanted, fixed in 4% paraformaldehyde (PFA), and processed for histology and hematoxylin and eosin (H&E) staining. The histological sections were imaged with a Nikon E800 upright microscope, from which the thickness of inflammatory region was determined. The degree of inflammation was subsequently assessed by a blinded histopathology expert.

Example 15. Physical Interpenetration of Bridging Polymer

Interpenetration of the high density primary amine polymer into the bulk matrix of the TAs was imaged using FITC labeled chitosan and confocal microscopy. The FITC-chitosan was dissolved into MES buffer to 2 wt % with pH adjusted to 6, and then the mixture of 20 μL was distributed on the surface of a hydrogel disk of diameter 6 mm with or without EDC/NHS. The incubation time was varied from 2 to 30 minutes, before aspirating the excess FITC-chitosan solution. Fluorescent microspheres of 20 μL volume were added onto the same hydrogel surface, followed by extensive rinsing with DI water for 30 seconds. The fluorescent microspheres carry carboxylate groups on their surface that can bind with the primary amines on the FITC-chitosan, forming amide bonds via carbodiimide chemistry. A confocal fluorescence microscopy (Zeiss LSM710) was used to image the gel surface, with the excitation wavelengths set to 490 nm for FITC and 588 nm for the fluorescent microspheres.

FIG. 21 (A) shows that FITC-chitosan was applied to the alginate/polyacrylamide hydrogel comprising the dissipative matrix, and allowed to diffuse into the gel. The photographs imaged by confocal fluorescence microscopy are shown in FIGS. 21 (B) and (C). As demonstrated in FIG. 21 (D), the high density primary amine polymer exhibited high mobility, as it interpenetrated with the hydrogel over the incubation time, forming an adhesive surface.

Example 16. In Vitro Cell Compatibility Test

The tough adhesive and cyanoacrylate were incubated separately in 1 mL DMEM containing 10% FBS at 37° C. for 24 hours, and the masses of the tough adhesive and the cyanoacrylate under incubation were fixed at ~22 mg. The tough adhesive was prepared by surface modifying an alginate-polyacrylamide hydrogel of 20 mg with 2 μL solution of chitosan and EDC/Sulfated NHS, in which the chitosan concentration was at 2 wt %, and the final concentrations of EDC and Sulfated NHS in the solution of the high density primary amine polymer (i.e., chitosan) were both 12 mg/mL. To further assess the cell compatibility of the compounds of the tough adhesive, conditioned medium was also prepared by incubating the alginate-polyacrylamide hydrogel of 20 mg and a 2 µL solution of chitosan and EDC/Sulfated NHS in medium as well. Human dermal fibroblasts were plated in 96-well plates ($1.2 \times 10^4$ cells per well, n=5 per experimental condition). Cells were treated with each conditioned media (200 µL per well) and incubated for 24 hours at 37° C. and 5% $CO_2$. Cell viability was determined with a LIVE/DEAD Viability/Cytotoxicity kit for mammalian cells (ThermoFisher Scientific); An Olympus IX81 inverted microscope was used to image live cells with excitation/emission at 495 nm/515 nm, and dead cells at 495 nm/635 nm separately.

As demonstrated in FIG. 22, in the instant in vitro cell study, human dermal fibroblasts were able to maintain full viability after 24 hours culture in TA-conditioned medium.

Example 17. Hemostatic Dressing to Stop Bleeding

The biocompatible adhesives can be used as hemostatic dressing to stop heavy bleeding under uncontrolled hemorrhage conditions. A rodent liver laceration model was chosen to test the use of tough adhesives as hemostatic dressings. This example was carried out with Female Sprague Dawley rats (around 175 g). The animals were anesthetized via isoflurane by inhalation in chamber (4%), and then by ventilation (2%). A ventral midline laparotomy incision was created, and the left liver lobe was exposed, where a partial-thickness wound was created with a biopsy punch of 6 mm, followed by laceration with a scissor. Immediately after injury, the tough adhesive or the SURGIFLO hemostatic matrix (as a positive control) was applied on the site of the lesion (n=4). A negative control without any treatment was also included for comparison (n=4). During the procedure, the blood was carefully collected with filter papers at 2, 5 and 10 minutes, the total amount of the blood at each time point was weighed (FIG. 25). The abdomen was closed 15 minutes after the wound creation. The animals were allowed to recover from anesthesia before returning to the cage. At 2 weeks, the animals were euthanized by $CO_2$ inhalation, and the implants as well as the surrounding tissue were explanted and further processed for histological analysis. Sectioning, paraffin embedding, and Hematoxylin-Eosin (H&E) staining was performed at the Rodent Pathology Core at Harvard Medical School, where a board-certified pathologist examined the histological sections.

Example 18. Bandages for Wound Management

All work was done with C57BL/6J mice (female, aged 6-8 weeks; Jackson Laboratories) and was carried out in accordance with the Institute for Animal Care and Use Committee, Harvard University, and National Institutes of Health and institutional guidelines. Mice were anesthetized, and a region of the dorsum was shaved. Two pieces of tough adhesive of 6 mm diameter were applied with a custom designed applicator for 2 minutes. Anesthesia was maintained with isoflurane (1-2%). For the use of wound dressing, a skin wound was created with a biopsy punch of 4 mm on the dorsum. The tough adhesive of 10 mm diameter was applied with gentle compression for 2 minutes. To slow down the water evaporation, Tegaderm film (3M) was further attached and fixed on the dorsum using suture or wound staples. The mice were returned to their cages after recovery from anesthesia. Videos were taken to assess the adhesion under the movement of mice. The attachment of the tough adhesives was monitored on day 1 and 7 (FIG. 26). A thermo-sensitive biocompatible adhesive based on IPNs of PNIPAM and alginate was also tested for wound management. The thermo-sensitive adhesive can shrink at the skin temperature, and further contract the wound edges to actively close up the wound. The efficacy of this active bandage was demonstrated in vitro with a rodent skin (FIG. 27). The mice were returned to their cages after recovery from anesthesia. Videos were recorded to assess the adhesion under the movement of mice.

Example 19. Injectable Adhesives for Cartilage Repair

This work was based on an injectable formulation of a biocompatible adhesive that consists of UV curable PEG-diacrylate polymers and alginate. A tissue model was created by punching a cylindrical defect on a cartilage disc explanted from a porcine articular cartilage. The inner surface of the cartilage defect was treated with the mixture of the primary amine polymers and the coupling agent (i.e. chitosan and EDC plus sulfo-NHS), and followed by injection of the injectable adhesive. A 5-minute exposure of UV light was applied to cure the adhesive, forming a repaired cartilage. The efficacy was accessed by compression tests, which showed the cartilage discs repaired with the injectable adhesive recovered around 80% stresses at the 20% strain (FIG. 28).

Example 20. Lung Sealant

A biocompatible adhesive in the form of a preformed patch can be used to repaired a lung defect. The adhesion on lung surfaces was demonstrated with a porcine lung, where a thin film of the adhesive adhered strongly and exhibited high deformability (FIG. 29). The adhesive was able to seal a defect on the lung and to accommodate the large deformation of the lung under a physiological function cycle.

Equivalents

Those skilled in the art will recognize, or be able to ascertain using no more than routine experimentation, many equivalents to the specific embodiments of the invention described herein. such equivalents are intended to be encompassed by the following claims. The contents of all references, patents and published patent applications cited throughout this application are incorporated herein by reference.

We claim:
1. A biocompatible adhesive system comprising:
a) a first component comprising a hydrogel comprising a first polymer network and a second polymer network, wherein said first polymer network comprises covalent crosslinks and said second polymer network comprises ionic crosslinks, wherein the first polymer network comprises polyacrylamide and the second polymer network comprises an alginate polymer;
b) a second component separate from the first component and comprising a high density primary amine polymer which is chitosan; and
c) a third component separate from the first component and the second component and comprising a coupling agent comprising 1-ethyl-3-(3-dimethylaminopropyl) carbodiimide (EDC, EDAC or EDCI) and optionally N-hydroxysuccinimide (NHS),
wherein after combination of the first component, the second component, and the third component, covalent bonds are formed between the hydrogel and a surface, and the system is characterized by an interfacial toughness of from about 500 J/m² to 5000 J/m².

2. The system of claim 1, wherein the alginate is comprised of a mixture of a high molecular weight alginate and a low molecular weight alginate.

3. The system of claim 2, wherein the ratio of the high molecular weight alginate to the low molecular weight alginate is about 5:1 to about 1:5.

4. The system of claim 1, wherein the first polymer network and the second polymer network are covalently coupled.

5. The system of claim 1, wherein the system further comprises a first therapeutically active agent, and optionally, a second therapeutically active agent.

6. The system of claim 5, wherein the first therapeutically active agent is encapsulated in or attached to the surface of the hydrogel.

7. The system of claim 5, wherein the first therapeutically active agent is encapsulated in or attached to the surface of the high density primary amine polymer.

8. The system of claim 5, wherein the first and second therapeutically active agents are independently selected from the group consisting of a small molecule, a biologic, a nanoparticle, and a cell, wherein the biologic is selected from the group consisting of a growth factor, an antibody, a vaccine, a cytokine, a chemokine, a hormone, a protein, and a nucleic acid.

9. The system of claim 1, wherein a device is encapsulated with the hydrogel and the high density primary amine polymer and coupling agent are applied to the exterior surface of the hydrogel encapsulating the device.

10. The system of claim 9, wherein the device is a medical device selected from the group consisting of a defibrillator, a pacemaker, a stent, a catheter, a tissue implant, a screw, a pin, a plate, a rod, an artificial joint, a pneumatic actuator, a sensor, an elastomer-based device, and a hydrogel based device.

11. The system of claim 1, wherein the system is characterized by an interfacial toughness of from about 1000 $J/m^2$ to 5000 $J/m^2$.

* * * * *